(12) United States Patent
Branch et al.

(10) Patent No.: US 10,595,751 B2
(45) Date of Patent: *Mar. 24, 2020

(54) MULTIPLE TEST KNEE JOINT ANALYSIS

(71) Applicant: ERMI, Inc., Atlanta, GA (US)

(72) Inventors: Thomas P. Branch, Atlanta, GA (US); Shaun K. Stinton, Chamblee, GA (US); T. Christopher Madden, Atlanta, GA (US); Nathaniel K. deJarnette, Lilburn, GA (US)

(73) Assignee: RoboDiagnostics LLC, Atlanta, GA (US)

( * ) Notice: Subject to any disclaimer, the term of this patent is extended or adjusted under 35 U.S.C. 154(b) by 252 days.

This patent is subject to a terminal disclaimer.

(21) Appl. No.: 15/266,627

(22) Filed: Sep. 15, 2016

(65) Prior Publication Data

US 2018/0070862 A1  Mar. 15, 2018

(51) Int. Cl.
*A61B 5/00* (2006.01)
*A61B 5/11* (2006.01)
*A61B 5/103* (2006.01)

(52) U.S. Cl.
CPC .......... *A61B 5/1121* (2013.01); *A61B 5/4528* (2013.01); *A61B 5/4585* (2013.01); *A61B 5/1036* (2013.01); *A61B 5/1127* (2013.01); *A61B 5/702* (2013.01)

(58) Field of Classification Search
CPC ... A61B 5/1121; A61B 5/4585; A61B 5/4528; A61B 5/1036
See application file for complete search history.

(56) References Cited

U.S. PATENT DOCUMENTS

| | | | |
|---|---|---|---|
| 4,727,860 A * | 3/1988 | McIntyre | A61B 5/103 482/112 |
| 4,969,471 A | 11/1990 | Daniel et al. | |
| 5,935,086 A | 8/1999 | Beacon et al. | |
| 6,162,189 A | 12/2000 | Girone et al. | |
| 6,324,296 B1 | 11/2001 | McSheery et al. | |
| 7,291,119 B1 | 11/2007 | de Guise et al. | |

(Continued)

FOREIGN PATENT DOCUMENTS

| | | |
|---|---|---|
| WO | 2014076147 A2 | 5/2014 |
| WO | 2015121830 A1 | 8/2015 |

*Primary Examiner* — Sean P Dougherty
*Assistant Examiner* — David Joseph Fernandez-Fidalgo
(74) *Attorney, Agent, or Firm* — Lempia Summerfield Katz LLC

(57) ABSTRACT

A method includes obtaining test data during a plurality of joint tests, the test data being indicative of respective motion during each test, each test being implemented by a robotic testing apparatus that applies, during each test, a respective force oriented in a respective plane. Respective primary data indicative of respective movement in a respective degree of freedom disposed within the respective plane for each test is generated based on the test data. Secondary data indicative of concomitant movement during a first test of the plurality of tests is generated based on the test data, the concomitant movement being in a secondary degree of freedom other than the respective degree of freedom disposed within the respective plane for the first test, the concomitant movement arising from the respective applied force. A joint condition is determined based on the primary data for each test and the secondary data.

22 Claims, 14 Drawing Sheets

(56) References Cited

U.S. PATENT DOCUMENTS

| | | |
|---|---|---|
| 7,607,440 B2 | 10/2009 | Coste-Maniere et al. |
| 8,170,716 B2 | 5/2012 | Coste-Maniere et al. |
| 8,491,574 B2 | 7/2013 | Blumenkranz |
| 8,571,710 B2 | 10/2013 | Coste-Maniere et al. |
| 8,888,718 B2 | 11/2014 | Siston et al. |
| 2003/0109780 A1 | 6/2003 | Coste-Maniere et al. |
| 2005/0119661 A1 | 6/2005 | Hodgson et al. |
| 2005/0234332 A1 | 10/2005 | Murphy |
| 2006/0161051 A1 | 7/2006 | Terrill-Grisoni et al. |
| 2007/0055176 A1* | 3/2007 | Branch ................ A61B 5/1071 600/587 |
| 2009/0124936 A1 | 5/2009 | Branch et al. |
| 2010/0010506 A1 | 1/2010 | Murphy |
| 2012/0046540 A1* | 2/2012 | Branch ................ A61B 5/1036 600/415 |
| 2013/0041289 A1 | 2/2013 | Sena et al. |
| 2013/0282024 A1 | 10/2013 | Blumenkranz |
| 2013/0307955 A1 | 11/2013 | Deitz et al. |
| 2014/0081181 A1 | 3/2014 | Branch et al. |
| 2014/0135985 A1 | 5/2014 | Coste-Maniere et al. |
| 2014/0222157 A1 | 8/2014 | Al Hares et al. |
| 2014/0316242 A1 | 10/2014 | Musahl et al. |
| 2015/0201867 A1 | 7/2015 | Peindl et al. |

* cited by examiner

MULTIPLE TEST KNEE JOINT ANALYSIS

CROSS-REFERENCES TO RELATED APPLICATIONS

This application is related to the commonly assigned applications filed on Jun. 3, 2016, and entitled "Robotic Joint Testing Apparatus and Coordinate Systems for Joint Evaluation and Testing" (U.S. patent application Ser. No. 15/173,510), "Analysis System and Method for Determining Joint Equilibrium Position" (U.S. patent application Ser. No. 15/173,520), and "Robotic Knee Testing Apparatus and Patient and Apparatus Set-Up Methods" (U.S. patent application Ser. No. 15/173,536), the entire disclosures of which are hereby expressly incorporated by reference. The application is also related to the concurrently filed and commonly assigned application entitled "Off-Axis Motion-Based Analysis of Joints" (U.S. patent application Ser. No. 15/266,721), the entire disclosure of which is hereby expressly incorporated by reference.

BACKGROUND OF THE DISCLOSURE

Field of the Disclosure

The disclosure relates generally to robotic joint testing.

Brief Description of Related Technology

Knee injuries and ligament damage have been diagnosed using manual tests. These tests are performed by doctors or other medical personnel, i.e., clinicians, on the patient in order to detect and measure changes to joint play in order to diagnose damage to the knee ligaments or other knee joint support structures. There are a number of commonly known manual tests used to evaluate increased joint play associated with ligament injuries in the knee. The three most common tests, by their commonly used names, include the Dial test, the Lachman test, and the Varus-Valgus test. Because these tests are performed manually by individual medical personnel, these tests naturally are limited by the specific clinician's subjective evaluation. The subjective nature of the tests may hinder the precision or accuracy of any diagnosis of the extent of ligament lengthening (or damage), the change in ligament compliance or elastic resilience, i.e., stretchiness, changes in the bone structure, or combinations thereof.

The Lachman's test, or anterior-posterior drawer test at 30 degrees, is performed with a patient lying in a supine position. The clinician will bend the patient's knee joint at approximately 20 to 30 degrees. The clinician places one hand on the patient's upper thigh and their other hand below the upper part of the patient's calf. The clinician then applies upward and downward pressure under the patient's calf while opposing that force with downward and upward pressure on the patient's thigh. This induces an anterior and posterior translation between the patient's femur and tibia. The degree of translation is subjectively determined by the clinician to diagnose the injury or joint damage. In addition to the anterior and posterior motion, the clinician feels other off-primary axis motions occurring in the knee when applying the primary axis anterior-posterior load. Off-axis motions are those motions not oriented directly along the pathway of motion caused by the torque or other actuation directed to the limb. In other words, if the actuation is directed along the Y-axis in a positive and negative direction, off-axis motion would be oriented along translations along the X-axis or Z-axis, or along the rotations around all three axes.

The Dial test, or the 30 degree Tibial Axial Rotation test, is performed with the patient lying in the supine position with the knee at 30 degrees and the heel on the table. The foot is rotated in maximum internal rotation followed by maximum external rotation. The amount of rotation occurring both at the proximal tibia and at the foot is noted.

The Varus-Valgus Stress test can be performed under many conditions, the most common one having the patient supine and the lower leg cradled in the clinician's arms. Pressure is applied in abduction and adduction with movement at the foot while a hand stabilizes the femur. An assessment of both motion and separation of the joint space is noted along its medial and lateral joint line.

A fourth test combines all of the previous tests into a complex maneuver called the Pivot Shift test. The Pivot Shift test is similarly performed with the patient lying in a supine position. The leg is straightened out so that the knee joint is placed in full extension (x-axis rotation). A valgus or side-to-side outward rotation (y-axis rotation) force and an internal or twisting rotation (z-axis rotation) force is applied to the knee to allow the lateral tibia to slip anteriorly from underneath the lateral femoral condyle. As the knee is flexed or bent (x-rotation), the tibia is allowed to slip suddenly back underneath the femoral condyle. The clinician subjectively determines whether there is an abnormal external rotation (z-axis rotation) and posterior translation (y-axis translation) of the tibia with respect to the femur. The degree of shift that is felt or determined by the clinician represents to the clinician the relative increased translation (y-axis translation) of the lateral side of the knee with respect to the increased translation (y-axis translation) of the medial side of the knee. A sudden shift in the knee joint is felt by the clinician and represents the point at which the tibia bone slides from in front of the radius of curvature of the curved end of the femur back to its normal position under the femoral condyle. The Pivot Shift test is inherently subjective, difficult to accurately perform, difficult to teach, and ultimately difficult to quantify.

Grading each test usually involves the opinion of the physician placing the test into three categories, e.g., Grade I, Grade II or Grade III. For the pivot shift test, the grading depends upon the speed and intensity of the knee joint slipping back into place. For other tests, the grading represents the amount of motion detected by the clinician during the examination. For example, Grade I would be 0-5 mm of joint play. Grade II would represent 6-10 mm of joint play. Grade III would represent 11-15 mm of joint play.

The accuracy of an injury diagnosis provided by a clinician using currently known manual tests depends on the skill and experience of the clinician and their subjective determinations. A misdiagnosis can lead to unnecessary treatment or unnecessary delay in treatment, which may result in an increased risk for further injury or damage to the patient's knee joint.

A combination of these clinical examination tests can be used to diagnose lateral collateral ligament (LCL), medial collateral ligament (MCL), and posterior cruciate ligament (PCL), and other knee ligament injuries. Each manual test relies on grading the degree of length (or damage) increase in the ligament based on relative increase in joint play into three Grades or categories. There is no effort to grade the compliance or elastic resilience, i.e., stretchiness, of the ligaments using these manual tests. An expert clinician may instead describe the ligament in terms of its subjective feel to the clinician, e.g., by stating that the joint has a soft or hard endpoint. Also, a knee joint may have injury or damage to more than one ligament or structure. The more ligaments and structures of the knee joint that are damaged, the more complex it is for the clinician to perform a manual knee examination. This can make the full diagnosis less accurate and less precise.

Clinicians and surgeons manually examine the injured knee joint for altered or increased joint play. However, due to the variability in size of the patient, size and experience of the surgeon, and the potential degree or subtlety of an injury, consistent and reproducible reports of joint play between surgeons is not possible. Many reports have documented that, whether diagnosis is performed manually or even with manual arthrometers, the manual application of torque to the knee joint varies widely between clinicians due to differences in muscular strength and hand size for force application. This results in inconsistencies in the examination of joint play and, ultimately, the diagnosis made by the clinician.

Others have attempted to reduce the manual nature of such joint testing by applying an instrument to the knee joint during testing. The objective has been to mechanically or objectively quantify or measure a change in the structure of the knee after ligament damage. Several devices have been developed in attempting to more accurately quantify the extent of injury or relative displacement and compliance of a ligament in the knee. In one example, such devices have been developed by Medmetric Corp. These devices include the KT-1000 and KT-2000 models. The KT devices are intended to measure the anterior-posterior translation of the tibia with respect to the femur. The KT devices attach to the patient's tibia during testing.

The KT devices attempt to quantify the findings achieved by a clinician performing the Anterior-Posterior Drawer test at 30 degrees (Lachman's test) and the Anterior-Posterior Drawer test at 90 degrees. Force is applied to a handle on the device, which measures the force and delivers the amount of applied force to the clinician, which is indicated through sounds, such as a low pitched sound for a 15 pound force and a higher pitched sound for a 20 pound force. The applied force in the KT devices pulls anteriorly along the y-axis through a strap that wraps underneath the patient's calf. The translation is determined using a technique that measures the relative motion between a pad placed against the anterior tibia and a pad placed against the patella. The KT devices do not measure relative displacement or compliance in any of the other degrees of freedom in the knee. Also, quantified results from using the KT-1000 or KT-2000 devices have been found to not correlate with patient satisfaction.

Laxity testing in the past, both manual and instrumented, has been found to be inconsistent, both when testing the same patient from day to day and when two different examiners test the same patient. This is in part due to 1) the subjective nature, among examiners and among patients, of these prior examination and diagnosis techniques, 2) the complexity of the anatomy of the knee, 3) the lack of a system or method that is reliably repeatable to measure knee laxity, and 4) the accumulation of error introduced at different stages of an examination or diagnosis. Introducing significant error at any one or more steps during a test can greatly affect, and invariably reduce, the accuracy of the ultimate diagnosis. The degree of error may often overwhelm the ability to obtain an accurate diagnosis.

SUMMARY OF THE DISCLOSURE

In accordance with one aspect of the disclosure, a method includes obtaining test data for a joint during a plurality of joint tests, the test data being indicative of respective motion of the joint during each test of the plurality of tests, each test of the plurality of test being implemented by a robotic testing apparatus applied to the joint, the robotic test apparatus being configured to apply, during each test of the plurality of tests, a respective force oriented in a respective plane. Respective primary data indicative of respective movement of the joint in a respective degree of freedom for the joint disposed within the respective plane for each test of the plurality of tests is generated based on the test data. At least one test of the plurality of tests is alone not configured to detect a condition of the joint such that the respective primary data for the at least one test is not indicative of the condition. Secondary data indicative of concomitant movement of the joint during a first test of the plurality of tests is generated based on the test data, the concomitant movement being in a secondary degree of freedom for the joint other than the respective degree of freedom disposed within the respective plane for the first test, the concomitant movement arising from the respective applied force. The condition of the joint is determined based on an analysis of the primary data for each test of the plurality of tests and the secondary data.

In accordance with another aspect of the disclosure, a method includes obtaining test data for a knee joint during an anterior-posterior translation test, an external-internal rotation test, and a varus-valgus rotation test, each of which being implemented by a robotic testing apparatus applying a respective force to the joint, generating, based on the test data, respective primary data indicative of respective primary movement of the joint during the anterior-posterior translation test, the external-internal rotation test, and the varus-valgus rotation test, generating, based on the test data, secondary data indicative of concomitant movement of the joint during one or more of the anterior-posterior translation test, the external-internal rotation test, and the varus-valgus rotation test, the concomitant movement arising from the respective applied force, and determining a condition of the joint based on an analysis of the respective primary data for the anterior-posterior translation test, the external-internal rotation test, and the varus-valgus rotation test, and of the secondary data.

In accordance with yet another aspect of the disclosure, a system includes a memory in which input instructions, data processing instructions, and analysis instructions are stored, and a processor coupled to the memory and configured through execution of the input instructions to obtain test data for a knee joint during a plurality of joint tests, the test data being indicative of respective motion of the joint during each test of the plurality of tests, each test of the plurality of test being implemented by a robotic testing apparatus applied to the joint, the robotic test apparatus being configured to apply, during each test of the plurality of tests, a respective force oriented in a respective plane. The processor is configured through execution of the data processing instructions to generate, based on the test data, respective primary data indicative of respective movement of the joint in a respective degree of freedom for the joint disposed within the respective plane for each test of the plurality of tests, and to generate, based on the test data, secondary data indicative of concomitant movement of the joint during a first test of the plurality of tests, the concomitant movement being in a secondary degree of freedom for the joint other than the respective degree of freedom disposed within the respective plane for the first test, the concomitant movement arising from the respective applied force. The processor is configured through execution of the analysis instructions to determine a condition of the joint based on an analysis of the primary data for each test of the plurality of tests and the secondary data.

BRIEF DESCRIPTION OF THE DRAWING FIGURES

For a more complete understanding of the disclosure, reference is made to the following detailed description and accompanying drawing figures, in which like reference numerals may be used to identify like elements in the figures.

Figure 1:
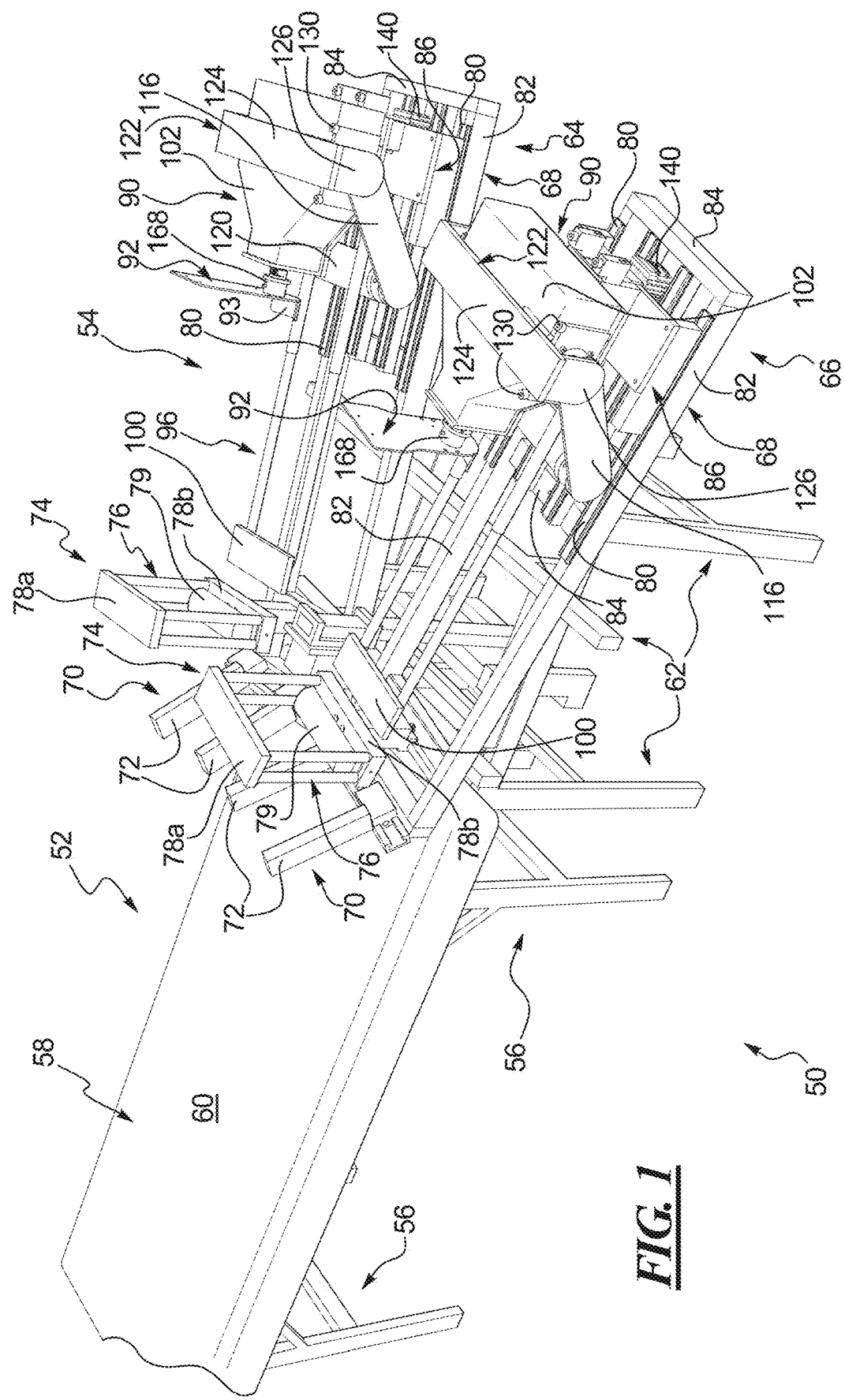
FIG. 1 shows a perspective view of one example of a robotic knee testing (RKT) apparatus according to the teachings of the present disclosure.

The disclosed methods, systems, and devices may assume various forms. Specific examples are illustrated in the drawing (and are hereafter described) with the understanding that the disclosure is intended to be illustrative, and is not intended to limit the invention to the specific examples described and illustrated herein.

DETAILED DESCRIPTION OF THE DISCLOSURE

Systems and methods for off-axis motion-based analysis of joints are described. Data indicative of the off-axis motion is generated from test data obtained via robotic joint testing. The robotic joint testing imparts or applies a force oriented in one or more primary degrees of freedom for the joint. The applied force(s) cause movement in the primary degree(s) of freedom. The primary motion in each primary degree of freedom is coupled with motions in the other degrees of freedom for the joint. Each applied force thus causes concomitant or secondary movement in one or more other degrees of freedom. For example, when a knee joint is flexed (flexion/extension rotation), there is also rotation about the long tibial axis (internal/external rotation). Other possible concomitant movements may involve rotation about the other orthogonal axis (abduction/adduction or varus/valgus rotation), as well as translation along any of the axes (medial/lateral translation, anterior/posterior translation, and compression/distraction translation). The concomitant movement arising from the imparted force may thus be considered off-axis motion. The robotic joint testing generates force (e.g., torque) and position data indicative of the off-axis motion. A condition of the joint is then determined based on an analysis of the generated data.

The use of robotic test apparatus to capture the test data used to generate the off-axis motion data avoids having to rely on a clinician or physician to detect off-axis motion during a manual examination. It may difficult for the physician to feel off-axis motion while attempting to drive and gauge the primary motion. For instance, the off-axis motion may be much more subtle than the primary motion. Moreover, differences in the force applied by the physician may lead to widely varying off-axis results.

Off-axis movement detection and analysis is supported by a test framework and apparatus that considers the bones of the joint as independent, free bodies. A free body kinematic framework allows for completely independent movement and measurement of motion between the bones of the joint. For example, in a test framework for a knee joint, there are no restrictions on the relative movement of the tibia and femur. The free body kinematics framework allows each of these free bodies to move in any manner without being influenced by the other free body to which the relative motion is occurring. Anatomically defined coordinate systems are defined in this framework, but the coordinate systems are allowed to move in three-dimensional space in any manner.

The free body kinematics of the test framework presents several advantages. For example, any point on one rotating free body has the same rotation in relationship to any point on the other rotating free body. The rotation between the free bodies is also independent of the selection of an origin for each coordinate system. As a result, the rotational test results are not biased via the selection of the origin for the test framework. The origin may also be selected so as to provide the best world view for translation measurements.

The free body kinematic framework establishes a technique for processing the test data generated by position sensors of the robotic test apparatus. For instance, a rotational matrix may be used to describe motion between the two bodies. The free body kinematics framework thus allows the test data to be processed to describe movement in all six degrees of freedom—three translations (e.g., anterior/posterior, medial/lateral, and compression/distraction) and three rotations (e.g., roll, pitch, and yaw). The robotic testing apparatus described herein is thus capable of producing data indicative of movement in any or all of the six degrees of freedom.

The data indicative of movement in any or all of the six degrees of freedom is then evaluated, processed, or otherwise analyzed. Such analysis may be useful in situations in which the primary motion along or around one axis does not supply sufficient information to diagnose a ligament injury or otherwise determine a condition of the joint under test. The off-axis information may be used to provide a more comprehensive assessment of joint condition. Such off-axis information is lost in other joint coordinate systems, such as the body-fixed coordinate system described by Grood and Suntay.

In examples involving the testing of a knee joint, a load or torque may be applied to the tibia from a position distal to the foot. While the test is in progress, position data and torque data are collected via the robotic testing apparatus for each of the six degrees of freedom, i.e., X-translation, X-rotation, Y-translation, Y-rotation, Z-translation and Z-rotation. The primary motion of the tibia occurs along or about which the axis the load or torque is oriented. For example, if the load is applied around the tibial Z-axis, then the primary motion during the test is the tibial motion in internal and external rotation, or around the tibial Z-axis. The secondary motions are in the other five degrees of freedom not in the primary motion, e.g., X-translation, Y-translation, Z-translation, X-rotation and Y-rotation. The analysis may be based on data indicative of any combination of these secondary motions. For example, in connection with anterior-posterior primary movement of a knee joint, the secondary motions involving flexion/extension and compression/distraction may be analyzed.

In some cases, multiple forces are concurrently applied to the joint. Each force is oriented and associated with a respective primary degree of freedom. Motion in any one or more the primary or secondary degrees of freedom may be analyzed in these cases.

The position and torque data may be processed to varying degrees in preparation for analysis. In some cases, position and torque information is evaluated. For example, the extent or range of motion for one or more degrees of freedom is analyzed. Alternatively or additionally, the position and torque information may be combined into one or more load-deformation curves or other data for the degree of freedom(s). Such load-deformation data is then analyzed to determine the condition(s) of the joint under test. For instance, when all six of the load-deformation curves are combined into one data set, the data set can be said to describe the kinetic/kinematic function unique to one knee. Each load-deformation curve represents a principle component in the analysis of function of that one knee. From each two-dimensional plot of the load-deformation curve, single features or a family of features can be extracted or otherwise determined. The features can collectively describe each of these principal components. Furthermore, each load-deformation curve can be used to estimate a first and second order derivative curve. Each one of these derivative curves can contain information that can be singularly separated out as a feature to describe unique characteristics of that particular principle component. Various collections of these 'descriptors' or 'features' can be utilized to develop a profile or other dataset defining or otherwise representative of a particular ligament injury or other joint condition.

The load-deformation curve data may involve the torque or force applied in the primary degree of freedom. The position data for the off-axis motion may be plotted against the applied torque levels. Alternatively or additionally, the position data is plotted against the resulting torque or force measured in the secondary degree(s) of freedom. The position data for the off-axis motion may be plotted against any of the measured reaction forces generated as a result of that applied torque. The measured reaction force may correspond with the force exerted by the joint on a torque sensor configured to measure torque in a degree of freedom other than the one associated with the applied torque.

In some cases, the joint testing includes multiple tests involving forces oriented in different planes. Each test is associated with a respective degree of freedom disposed within the respective plane. Data indicative of the primary movement for each test is generated, along with data indicative of one or more of the concomitant or secondary motions arising during one or more of the tests. The subsequent analysis may then take into account the data generated from all of the tests. In knee joint examples, the tests may include various combinations of an anterior/posterior translation test, an external/internal rotation test, and a varus/valgus rotation test. The examples of robotic test apparatus described below are capable of testing in all three of the planes associated with those tests. It may be useful to test in all three planes because knee instability may be present in only one (or some) of the planes and, thus, be evident in only one of the tests.

Testing in multiple planes is useful to obtain a complete and accurate assessment of joint condition. For example, with knee joints, there may be little to no correlation in laxity between any of the testing planes. Thus, in some cases, one test cannot predict the outcome of the other tests. As a result, a normal result in one test does not lead to a greater likelihood of a normal result in another test. Thus, in some cases, a particular test alone is not configured to detect a particular condition (e.g., an abnormal condition such as an injured ligament). As a result, the test data generated via that particular test is not indicative of the condition. However, analysis of the test data from multiple tests (e.g., tests in all three planes) is nonetheless capable of determining the condition.

The data indicative of the primary and secondary movement may be combined with other information to evaluate or assess the condition or status of the joint under test. A profile of characteristics may be compiled to avoid undue reliance on a single factor, parameter, or characteristic. The profile may then be compared with preset profile data associated with normal and abnormal joints to determine, for instance, a particular type of surgical or non-surgical treatment. A wide variety of information other than characteristics derived from the curve may be incorporated into the profile, including, for instance, data not captured by the robotic testing apparatus, such as characteristics of the bone structure(s) of the joint.

Various combinations of descriptors or other features of a joint under test can be analyzed together as a mechanical system. Under the guidelines of control theory, conditions of the joint can be tested or evaluated using the descriptors or features in a procedure to determine when and if the joint is or will become unstable, e.g., when the distal femur and the proximal tibia do not articulate in a normal or 'healthy fashion' or when patients have subjectively described instability or when a clinician can reproduce the aforementioned positive 'pivot shift' test.

Although described in connection with a number of examples involving knee testing and evaluation, the disclosed systems and methods are not limited to a particular type of joint. The systems and methods are also not limited to particular types of tests. The nature of the tests may vary considerably in conjunction with the type of joint being assessed or evaluated. The data from any number of tests may be combined or synthesized.

Although described in connection with a number of examples of a robotic testing apparatus, the source of the data obtained by the disclosed systems and methods may vary. A variety of different test devices and equipment may be used in conjunction with, and/or as part of, the disclosed systems and methods. As described below, the nature of the data acquired by the test equipment may vary as well.

Turning now to the drawings, FIG. 1 shows a robotic testing apparatus 50 in accordance with one example. In this case, the robotic testing apparatus 50 is an RKT apparatus. Details regarding examples of the RKT apparatus 50 are described in U.S. Patent Publications Nos. 2014/0081181 and 2012/0046540, the entire disclosures of which are hereby incorporated herein by reference.

The RKT apparatus 50 of FIG. 1 generally has a patient support or, as identified herein, a table assembly 52. The RKT apparatus 50 also has a robotic mechanism or limb manipulation device, identified for ease of description herein as a robot 54, positioned at one end or edge of the table assembly. The table assembly 52 in this example has a supporting frame that is identified herein as a base 56 beneath a patient platform 58. The base 56 is configured to rest on a floor or surface and to support the patient platform 58 above the floor. The patient platform 58 can include a substantially rigid or sturdy panel (not shown) capable of holding and supporting a patient thereon. The panel can be affixed to or otherwise supported by the base 56. The panel of the patient platform 58 can underlie a padded surface 60, which can include a textile or fabric material that covers a cushion, padding, or the like (also not shown).

As will be evident to those having ordinary skill in the art, the configuration and construction of the table assembly 52 can vary considerably from the example disclosed, illustrated, and briefly described herein. The base 56 and/or the patient platform 58 can each be altered in size, shape, orientation, height, construction, materials, and the like. The base can include multiple legs and frame elements that are assembled or connected to one another, as in the illustrated example. Alternatively, the base can be formed as one unitary support element. The patient platform can also be formed of multiple components and can be fastened to or otherwise attached to the base. Alternatively, the patient platform can an integral, one piece fabricated structure and can be fabricated as part of the base or attached thereto. The table assembly need not be a table, but instead can be a chair, a suspension system, or other suitable patient support that is capable of properly positioning and retaining a patient relative to the robot 54 for testing and examination. The table assembly 52 can further include additional features, though not disclosed or described herein, that may be used to assist in positioning a patient on the platform, to assist in maintaining a patient's position on the platform, or to otherwise enhance patient comfort or improve performance of the table assembly, the RKT apparatus, or both.

With reference to FIG. 1, the robot 54 in this example can include a main or primary support frame structure, identified herein for ease of description as a frame 62. The frame 62 may optionally be coupled to, a part of, or otherwise supported by or connected to a portion of the base 56 of the table assembly 52, as shown in FIG. 1. Alternatively, the frame of the robot 54 can be an extension of, connected to, or otherwise supported by a portion of the patient platform 58. In a further alternative, the frame can be some combination of such supporting structures and arrangements or can be a completely separate structure. In any case, the frame 62 in this example supports and positions the robot 54 of the RKT apparatus 50 at one end of the table assembly 52.

Figure 2:
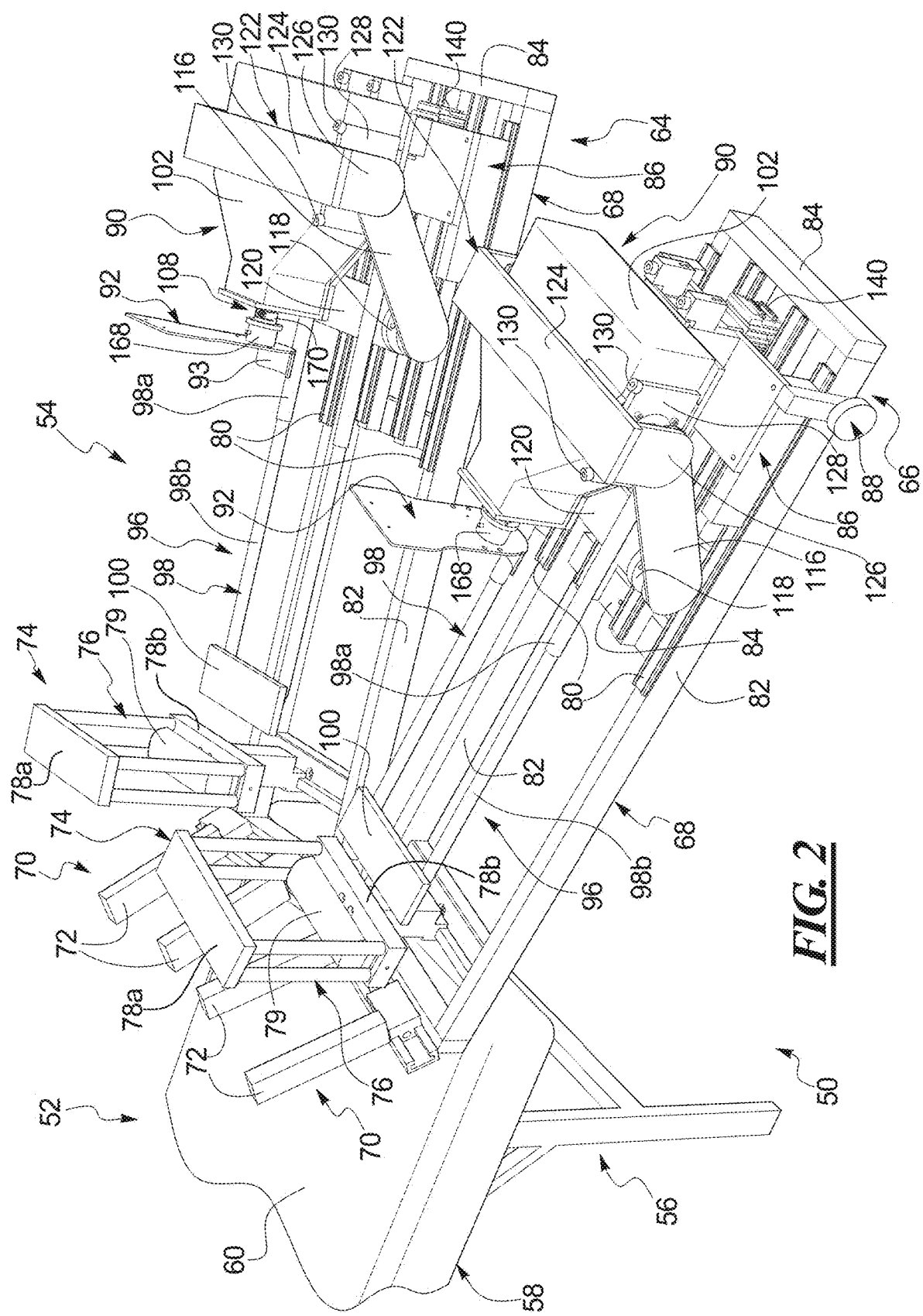
FIG. 2 shows an enlarged view of a limb evaluation device or robot of the RKT apparatus of FIG. 1.
Figure 3:
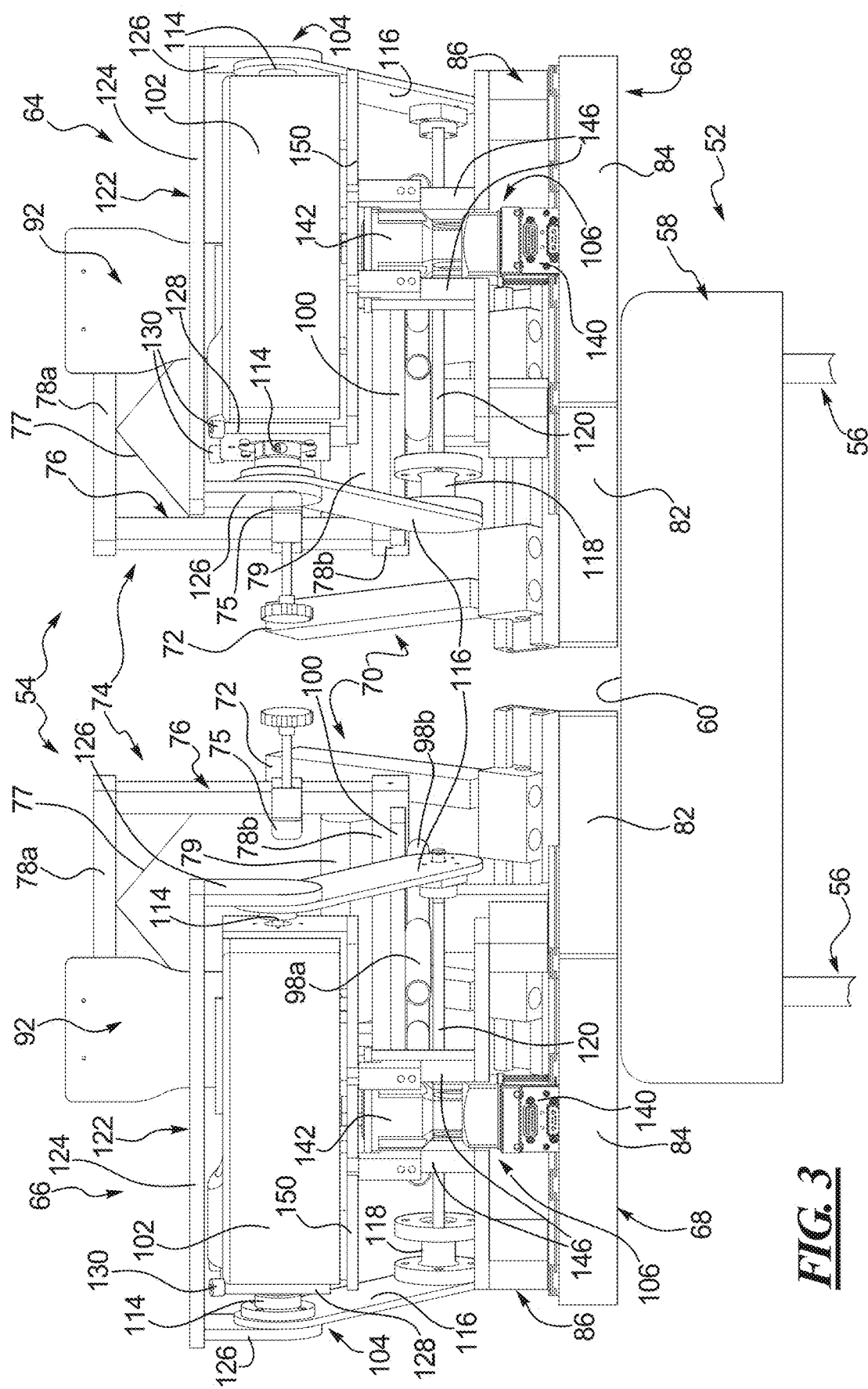
FIG. 3 shows an end view of the robot when viewed from the right hand side in FIG. 2.

In the disclosed example and with reference to FIGS. 2 and 3, the robot 54 has a left leg testing and evaluation mechanism and a right leg testing and evaluation mechanism, each mechanism respectively identified herein as a left leg portion 64 and a right leg portion 66 of the robot. The left and right leg portions 64, 66 have substantially the same construction, and may be essentially identical, if desired, and each is constructed to support and evaluate a left leg and right leg, respectively, of a patient. Therefore, like reference numerals are used herein to identify common parts of each of the two leg portions 64, 66 that have the same construction. The left and right leg portions 64, 66 each have a sub-frame 68 that, in this example, is supported by the frame 62 of the robot 54. Each sub-frame 68 supports the components and parts of the corresponding left and right leg portions 64, 66. For ease of description, the right leg portion 66 of the robot 54 is described in more detail below with the understanding that the left leg portion 64 has or may have the same overall construction. Differences between the two leg portions are identified herein, if and as needed. It is possible that an RKT apparatus is provided that has only one leg portion for evaluating only one leg of a patient at a time. However, in the disclosed example, the RKT apparatus 50 has left and right leg portions 64, 66.

Figure 4:
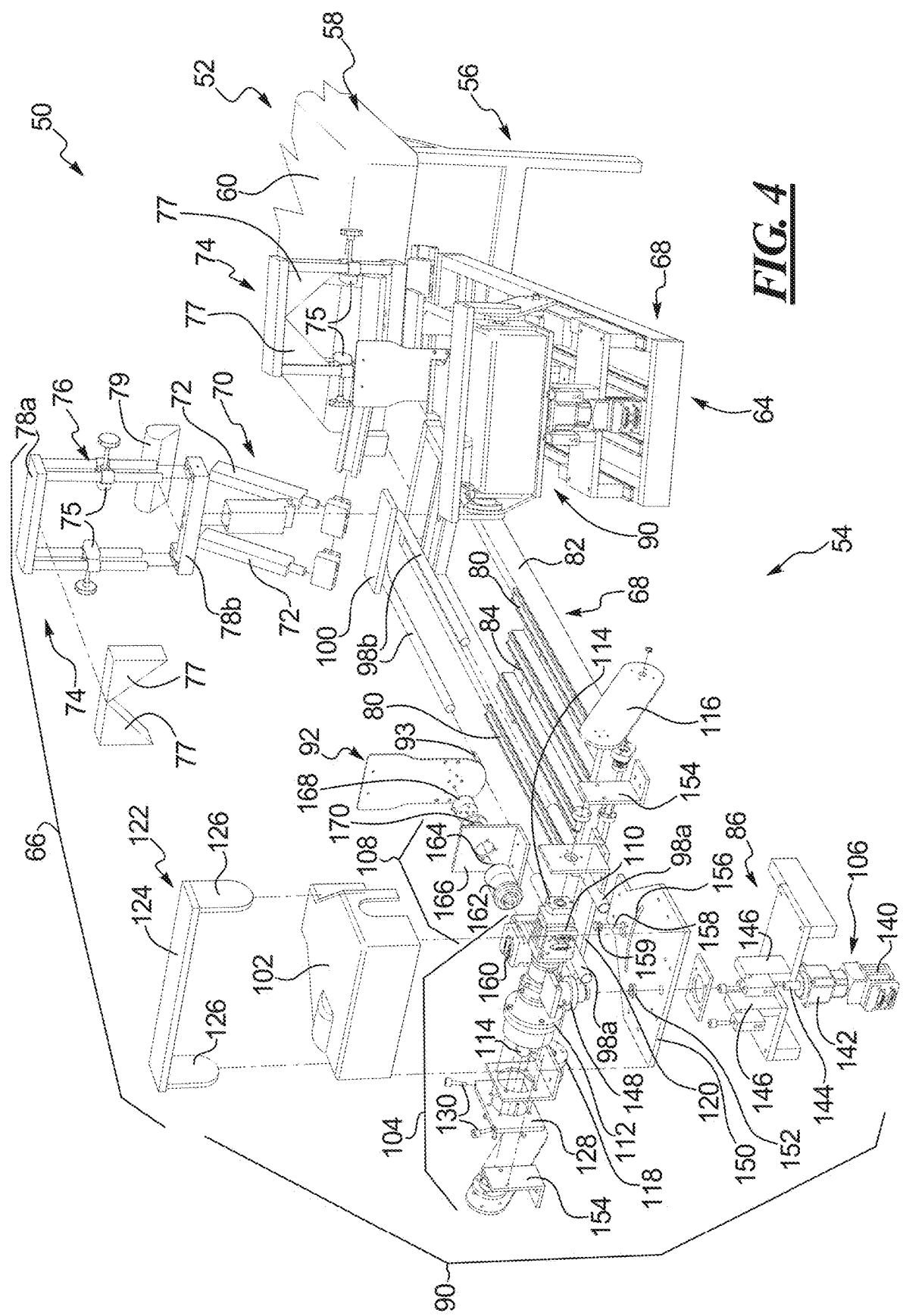
FIG. 4 shows a partial exploded view of the robot of FIG. 2 with the right leg portion of the robot exploded.
Figure 5:
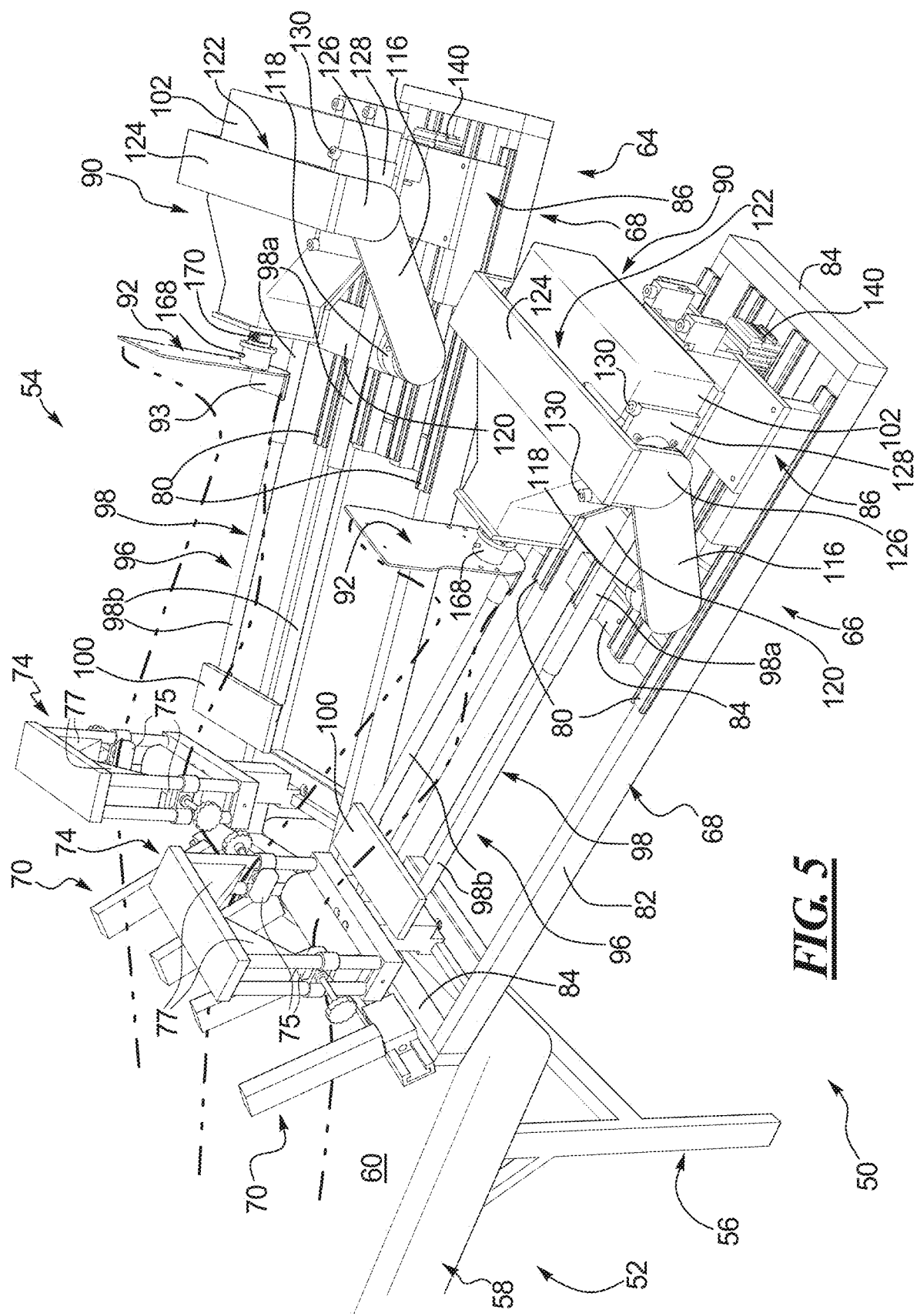
FIG. 5 shows the robot of FIG. 2 and depicts left and right legs of a patient positioned relative to the left and right leg portions of the robot.

As depicted in FIGS. 2-4, the right leg portion 66 has a thigh stabilizer 70 positioned closest to the table assembly 52. The thigh stabilizer 70 can be mounted to the frame 62 or the sub-frame 68, or can be otherwise mounted to a portion of the RKT apparatus 50 in a manner suitable for use as described below. The thigh stabilizer 70 can be constructed so as to be positionally adjustable to accommodate a wide range of patients of different size. Alternatively, the thigh stabilizer 70 can be mounted in a fixed position relative to the table assembly 52, whereby the position of the patient on the table assembly 52 and relative to the thigh stabilizer 70 might be adjustable. In either embodiment, the thigh stabilizer 70 should be positioned or positionable to contact a portion of a patient's upper leg or thigh above the knee, as depicted in FIG. 5.

The thigh stabilizer 70 in this example has a pair of femur clamping elements 72, i.e., medial and lateral clamping elements, that are laterally spaced apart and width-wise adjustable relative to one another. Though not shown herein, the clamping elements can include a pad or pads on the thigh facing surfaces, if desired, to provide a degree of comfort for a patient. The femur clamping elements 72 can be side-to-side adjusted in order to clamp or otherwise securely hold a patient's right femur and thigh in a substantially fixed side-to-side position during testing, evaluation, or treatment, as described below. If the thigh stabilizer 70 is positionally adjustable, it should be capable of being secured in a fixed selected position, once properly adjusted for a given patient, relative to the table assembly 52 and/or robot 54 during testing, evaluation, or treatment. The configuration and construction of the thigh stabilizer 70 can vary considerably from the example shown herein. The clamping elements 72 can be replaced by other suitable securing or clamping devices or elements, and the mechanisms to adjust and secure the thigh stabilizer 70 can also vary.

The right leg portion 66 also has a knee stabilizer 74 positioned adjacent the thigh stabilizer. The knee stabilizer 74 can also be mounted to the frame 62 or the sub-frame 68, or can be otherwise mounted to a portion of the RKT apparatus 50 in a manner suitable for use as described below. The knee stabilizer 74 can optionally also be constructed so as to be lengthwise or longitudinally positionally adjustable to accommodate a wide range of patients of different size. The knee stabilizer can also be side-to-side adjustable as well. Alternatively, the knee stabilizer 74 can be mounted in a fixed position relative to the table assembly 52, whereby the position of the patient on the table assembly 52 and relative to the knee stabilizer 74 may be adjustable. In either embodiment, the knee stabilizer 74 should be positioned or positionable to contact the knee or patella at the lower end of a patient's femur and thigh, as depicted in FIG. 5.

The knee stabilizer 74 acts as a knee or patellar clamp and can include a framework 76 arranged to surround and clamp onto a patient's joint or knee. The knee stabilizer 74 in this example has a pair of patellar clamping elements, including an upper clamping element 78a and a lower clamping element 78b that are vertically spaced apart and adjustable relative to one another along the framework 76. The patellar clamping elements 78a, 78b can be vertically adjusted in order to clamp or otherwise securely hold the lower end of a patient's right femur and patella in a substantially fixed vertical position during testing, evaluation, or treatment, as described below. If the knee stabilizer 74 is positionally adjustable, it should be capable of being secured in a fixed selected position, once properly adjusted for a given patient, relative to the table assembly 52 and/or robot 54 during testing. The configuration and construction of the knee stabilizer 74 can vary considerably from the example shown herein. The patellar clamping elements 78a, 78b can be replaced by other suitable securing or clamping devices or elements and the mechanisms to adjust and secure the knee stabilizer 74 can also vary.

Though not shown in all of the figures, the knee stabilizer 74 can include a plurality of substantially rigid and/or resilient pads for holding and restraining the knee and patella of a patient. In one example, the knee stabilizer knee can include a pair of side-to-side opposed Varus-valgus pads 75 that are adjustable, as shown and described below, toward and away from one another across the framework 76. The knee stabilizer 74 can also include one or more upper pads 77 on the upper clamping element 78a and a lower pad 79 on the lower clamping element 78b. The pads 75, 77, and/or 79 can be configured and arranged to lie adjacent the patient's knee. The various pads 75, 77, and 79 can be configured to prevent the framework 76 and the patellar clamping elements 78a, 78b from directly contacting the patient's knee, but also to assist in restraining the knee and inhibiting movement during testing. The pads 75, 77, and/or 79 can be solid, hollow, pressurized, hydraulically filled, pneumatically filled, or the like and can be rubber, foam, or otherwise formed of suitable materials. In one example as shown, the pad or pads 77 on the upper patellar clamping element 78a can be configured to define a V-shape within the framework 76. The patient's leg can then be captured within the V-shape as the upper and lower patellar clamping elements 78a, 78b are drawn toward one another to capture and hold the patient's leg still during a procedure. In particular, the stabilizer 74 and these pads 77 can aid in constraining the patella during testing. The Varus-valgus pads 75 can also be adjusted to restraint movement of the patient's knee in a side-to-side direction during at least Varus-valgus testing, as described below.

The thigh stabilizer 70 and/or the knee stabilizer 74 may be mechanically adjustable to manually fit and accommodate different sized patients. In one alternative, the thigh stabilizer 70 and/or the knee stabilizer 74 may be electrically operable to adjust the femur clamping elements 72, the patellar clamping elements 78a, 78b, respectively, or both. In another alternative example, the femur clamping elements 72 and/or the patellar clamping elements 78a, 78b may be pneumatically or hydraulically operable to adjust the thigh and knee stabilizers 70 and 74. In yet another alternative, the thigh stabilizer 70, the knee stabilizer 74, or both, may include two or more such systems or mechanisms for adjusting the respective clamping elements.

The thigh stabilizer 70 and/or femur clamping elements 72 and the knee stabilizer 74 and/or framework 76 and patellar clamping elements 78a, 78b can be formed of metal, plastic, or other suitable materials. The thigh and knee stabilizers 70 and 74 can vary in shape, configuration and construction, as desired. The thigh and knee stabilizers 70 and 74, in combination, are intended to secure a patient's leg in order to hold the femur and patella in a vertically (knee stabilizer) and laterally (thigh stabilizer) fixed position during a test, evaluation, or treatment cycle. Features and aspects of the disclosed thigh and knee stabilizers 70 and 74 can vary considerably while accomplishing this objective.

In this example as shown in FIGS. 2 and 4, the sub-frame 68 is configured to define or carry one or more slide tracks 80. The track or tracks 80 can be carried on the free end of the sub-frame 68 that is distal or spaced from the table assembly 52. The sub-frame 68 is formed having a plurality of rails 82 that extend lengthwise and having one or more cross-members 84 that extend laterally between the rails. The tracks 80 can be formed as an integrated part of the rails 82 or other sub-frame components or, as in this example, can be separately mounted to or supported by the rails and/or cross-members 84. One or more trucks or carriages, hereinafter a sled assembly 86 is mounted on or supported by the sub-frame 68 and is slidable along the tracks 80. The sled assembly 86 can slide along the tracks 80 to adjust the position of various parts of the RKT apparatus 50, as described further below. The sled assembly 86 can include a locking mechanism 88 (shown only in FIG. 2) to secure the sled assembly in a desired or selected position along the tracks 80. The locking mechanism 88 can vary in construction and position on the apparatus, as long as it can adequately secure the sled assembly at a selected position. Adjustment of portions of the RKT apparatus 50 can be achieved in other ways. In one example, the RKT apparatus can be mounted to a lift that can raise or lower the apparatus, or portions thereof, and that can slide or roll the robotic components relative to the table assembly 52, either eliminating or altering the need for the tracks 80 and rails 82.

As depicted in FIGS. 2-4, the right leg portion 66 further includes a tibia positioning assembly 90 that is mounted on the sub-frame 68. In this example, the tibia positioning assembly 90, or at least a portion of the assembly, is carried on the sled assembly 86. Thus, the tibia positioning assembly 90, or at least a portion thereof, is slidable lengthwise along the tracks 80 of the sub-frame 68 on the sled assembly 86, and thus is movable relative to the table assembly 52 and/or to the thigh and knee stabilizers 70 and 74.

In general, the tibia positioning assembly 90 has a foot holder, which in one example can be a foot plate 92, as in this example. The foot plate 92 has a heel stop 93 at the bottom edge of the foot plate that faces upward and has a contact surface 94 that faces toward the thigh and knee stabilizers 70 and 74. The tibia positioning assembly 90 also has a tibia rod device 96 with one or more rods 98 and a calf contacting or loading portion, which in one example can be a calf plate 100 as in this example. The calf plate 100 is disposed at or near a distal end of the tibia rod device 96. The one or more rods 98 can be lengthwise adjustable. In this example as shown in FIGS. 2-4, the tibia rod device 96 has two tibia rods 98, each of which has two telescoping segments including a fixed segment 98a and a slidable segment 98b that permit length adjustment of the rods 98. Though not shown or described in detail herein, the rods 98 may include a locking mechanism of a suitable type, such as holes and set screws, VALCO ball devices, or the like on one or both of the segments 98a, 98b, that can lock the adjusted rods at a selected length. The telescoping segments permit adjustable positioning of the calf plate 100 relative to the foot plate 92 to accommodate different sized patients. During use, the calf plate 100 lies under and contacts a patient's calf below the knee and the foot plate 92 bears against the sole of the patient's foot. The foot plate 92 can be configured to physically constrain and hold the foot of a patient against the contact surface 94. In one example, though not shown herein, the foot plate 92 can employ one or more straps that secure the patient's heel against the heel stop 93 and the sole of their foot to the foot plate 92. Likewise, the calf plate 100 can be configured to physically constrain the patient's leg to the calf plate, as described below for certain tests, or can merely lie against and under the patient's calf while not being otherwise secured to the leg for other tests.

Figure 6:
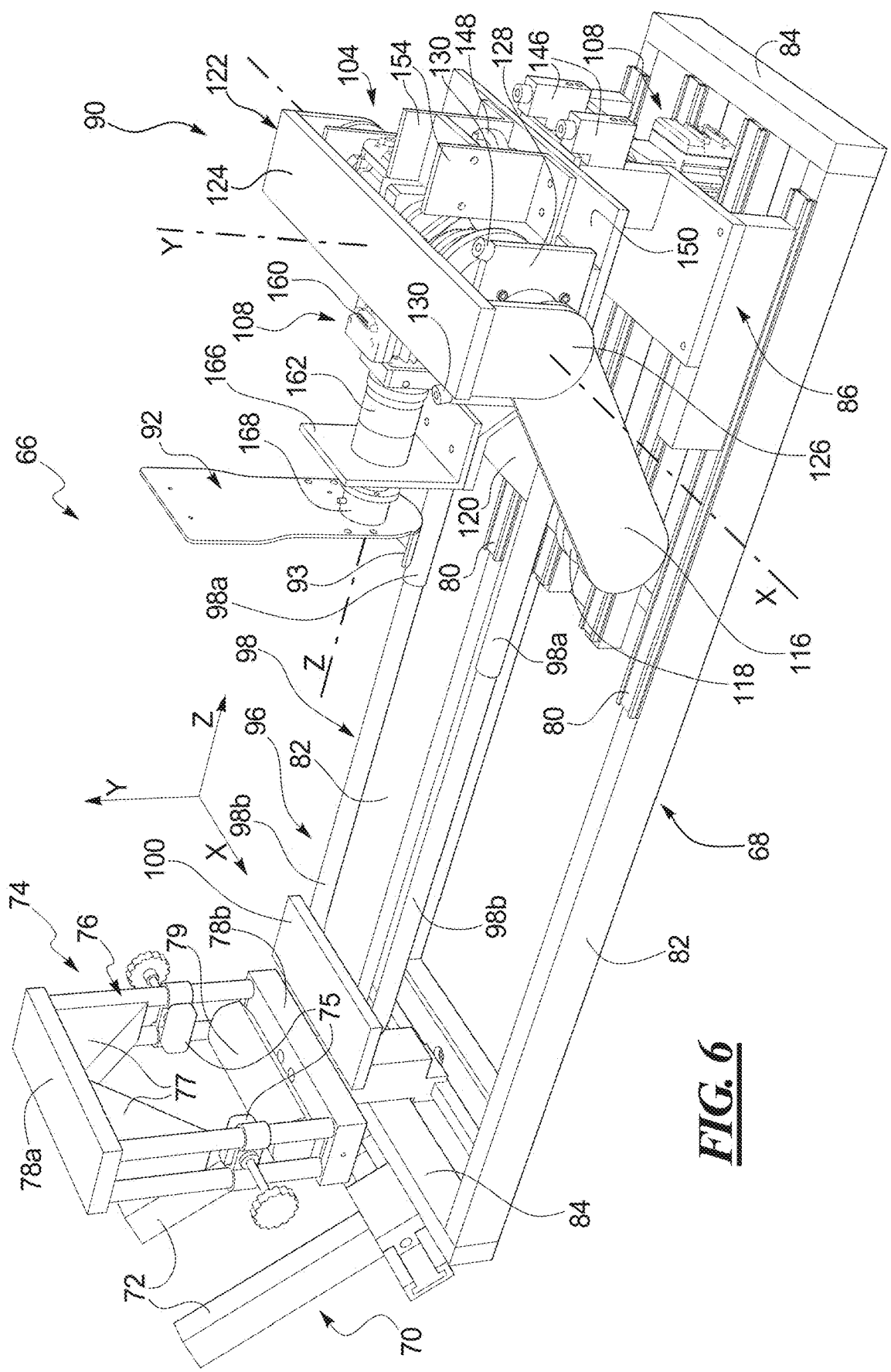
FIG. 6 shows the right leg portion of the robot of FIG. 2 and depicts an X-Y-Z coordinate system defined by the right leg portion.

With reference to FIGS. 4 and 6, the tibia positioning assembly 90 has a drive system with a number of drive components configured to impart specific and controllable movements to the lower leg of a patient. In this example, a substantial number of the drive system components are housed within a shell or housing 102. In other examples, the drive system components may be exposed and the shell eliminated. The drive system in this example generally has a first drive, i.e., an X-axis drive 104 as identified herein, which is oriented to define and provide rotation about a first axis, i.e., an X-axis as identified herein, which in this example lies generally laterally across the tibia positioning assembly 90. The drive system also has a second drive, i.e., a Y-axis drive 106 as identified herein, which is oriented to define and provide rotation about a second axis, i.e., a Y-axis as identified herein, which in this example lies generally vertically through the tibia positioning assembly 90, though not quite intersecting the X-axis, as described below. The drive system further has a third drive, i.e., a Z-axis drive 108 as identified herein, which is oriented to define and provide rotation about a third axis, i.e., a Z-axis as identified herein, which in this example lies lengthwise along the tibia positioning assembly 90. The three axes define a coordinate system and this coordinate system is identified as an X-Y-Z coordinate system for the right leg portion 66 of the robot 54 in this example. The robot will also have a similar X-Y-Z coordinate system specific to the left leg portion 64, but independent of the coordinate system for the right leg portion 66.

In other examples, the RKT apparatus may be configured to test only one or two of anterior-posterior motion, Varus-valgus motion, or tibial rotation, instead of all three tests. In such cases, the drive system may include only one or two of the X-axis, Y-axis, or Z-axis drives instead of all three drives. The methods and procedures described herein may be modified to accommodate such robots that have fewer than all three drives. In other examples, the X-Y-Z axes of the aforementioned coordinate systems may all intersect with one another and may all be orthogonal to one another. In still other examples, none or only two of the axes may intersect and/or none or only two of the axes may be orthogonal to one another.

As shown in FIG. 4, the X-axis drive 104 can include a first motor, such as an electric motor 110, a gearbox 112, and an output shaft 114 that is driven by the motor and gearbox. The opposite ends of the output shaft 114 in this example are fixedly coupled to the upper ends of respective drive links 116 on opposite sides of the housing 102. Thus, as the output shaft 114 is rotated by the motor 110 and gearbox 112, the drive links 116 are also rotated about the X-axis. The drive links 116 in this example are oriented downward and forward from the X-axis. The lower end of one of the drive links 116 is coupled or fixed to an X-axis torque transducer 118. The torque transducer 118 is also coupled or fixed to one end of a cross-plate 120. The lower end of the other drive link 116 is fixed to the opposite end of the drive plate 120. The cross-plate 120 is coupled to, and extends laterally across, the right leg portion 66 forward of the X-axis between the drive links 116. In this example, the fixed segments 98a of the tibia rods 98 are fixedly mounted to and extend forward toward the knee and thigh stabilizers 70, 74 from the cross-plate 120, as shown in FIGS. 2 and 4.

Figure 7:
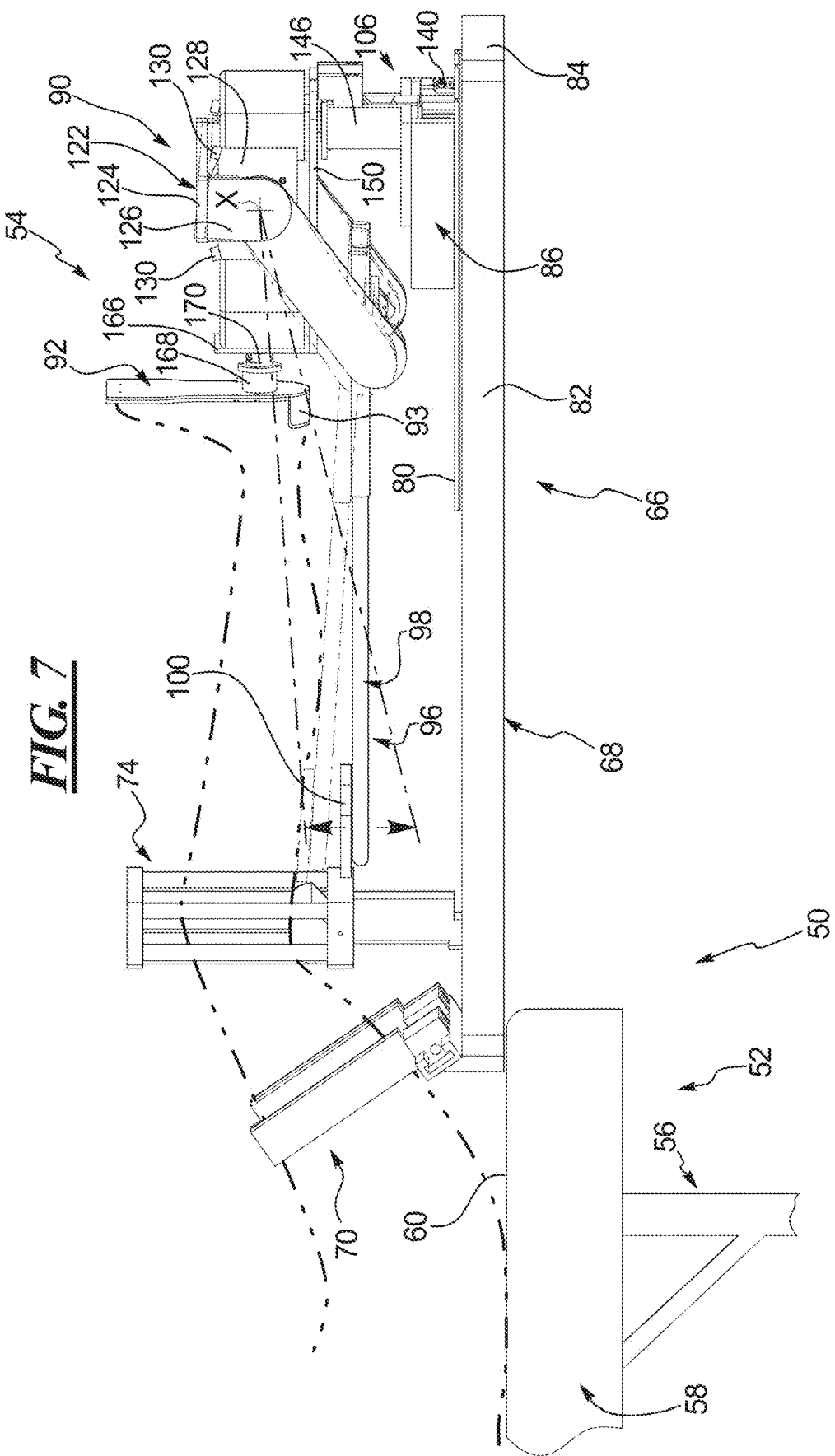
FIG. 7 shows a side view of the robot of FIG. 5 and illustrates anterior-posterior motion of the robot about the X-axis of the right leg portion of the robot.

With reference to FIG. 7, the X-axis drive 104 is configured to conduct an anterior-posterior or A-P test on a patient's knee. Position sensors can be applied to appropriate locations on the right leg of the patient. The X-axis drive 104 imparts force about the X-axis to initiate anterior-posterior motion in the tibia part of the knee joint relative to the fixed femur part of the knee joint of the patient, as shown in FIG. 7. The motor 110 can reversibly rotate the output shaft 114 through an arc about the X-axis whereby the upper ends of the drive links 116 are rotated through the same arc. This in turn moves, i.e., raises or lowers the lower ends of the drive links 116, which in turn raises or lowers the cross-plate 120 and the fixed segments 98a of the tibia rods 98. Movement of the fixed segments 98a of the tibia rods 98 raises or lowers the slider segments 98b and thus the calf plate 100 carried on the tibia rods 98. The X-axis torque transducer 118 measures the applied torque at the cross-plate 120 caused by the load applied at the calf plate 100 as the calf plate pushes up on the patient's tibia or the tibia rods 98 pull down on the patient's tibia. Motion and load data can be collected by a processor from the sensors relative to the motion in the patient's leg and from the X-axis torque transducer 118 relative to the torque or applied force.

The motor 110 and/or gearbox 112 can be designed to produce a limited range of travel, which may be substantially less than 360 degrees of rotations, in the output shaft 114. In addition or in the alternative, the X-axis drive 104 can also be designed to incorporate a mechanical travel limiter, if desired. In one example as shown in FIGS. 3, 4, 6, and 7, a yolk assembly 122 can be provided as part of the X-axis drive 104. The yolk assembly 122 has a top plate 124 extending over a top of the housing 102. The yolk assembly 122 also has a pair of side plates 126 extending down from the top plate 124. The side plates 126 can be affixed to the upper ends of the drive links or otherwise to the drive shaft 114 of the motor 110, so that the yolk assembly 122 also rotates with the drive shaft. A stop bracket 128 is disposed at one end of the motor 110 adjacent one of the yolk side plates 126. Two stops 130, i.e., fore and aft travel stops protrude upward from the stop bracket 128. The stops 130 are positioned and circumferentially spaced apart relative to the X-axis. The top plate 124 of the yoke assembly 122 is captured between the two stops and hits one of the stops to limit travel of the yoke assembly in either rotation direction. The radius of the side plates 126 and spacing of the stops 130 can thus limit rotational travel of the output shaft 114 to a specific arc, which mechanically limits the upward and downward travel of the tibia rods 98.

The above-described anterior-posterior movement components of the tibia positioning assembly 90 can vary considerably from the example shown and described herein. The yoke assembly 122 and stop bracket 128 can be eliminated or can take on different positions, configurations, and constructions. Instead, another mechanical stop mechanism can be employed. Likewise, the configuration and construction of the drive links 116, cross-plate 120, tibia rods 98, and calf plate 100 can also be varied. The mechanisms or devices that are used to secure a patient's leg to the tibia rods 98 and to the foot plate 92, if and when needed for testing, can also vary.

As shown in FIGS. 4 and 6, the Y-axis drive 106 can also include a second motor, which can also be an electric motor 140, a gearbox 142, and an output shaft 144 that is driven by the motor and gearbox. The gearbox 142 and motor 140 are fixed to the sled assembly 86 beneath the X-axis drive 104. Thus, the entire tibia positioning assembly 90, including the Y-axis drive components, can slide lengthwise along the sub-frame 68 to adjust the foot plate 92 position relative to the table assembly 52 and/or the thigh and knee stabilizers 70, 74. The motor 142 can be secured to a motor mount or bracket 146 that is carried on the sled assembly 86. A Y-axis torque transducer 148 is fixed to the output shaft 144 for rotation therewith. A pivot plate 150 can be sandwiched between a pair of thrust bearings 152 with the Y-axis drive below the pivot plate and the Y-axis torque transducer above the pivot plate. Support brackets 154 are secured to the top of the pivot plate 150 and the torque transducer 146 is fixed to the support brackets. The pivot plate 150 is disposed on top of the motor mounts 146 in this example and can rotate relative to the mounts and the sled assembly 86. The shell 102 can be secured to the pivot plate 150 to create an enclosure for the X-axis drive 104 and the Z-axis drive 108. Thus, as the output shaft 144 is reversibly rotated by the motor 140 and gearbox 142 about the Y-axis, as represented in FIG. 8, the shell 102, pivot plate 150, X-axis drive 104, Z-axis drive 108, foot plate 92, and tibia rods 98 will all rotate about the Y-axis.

Figure 8:
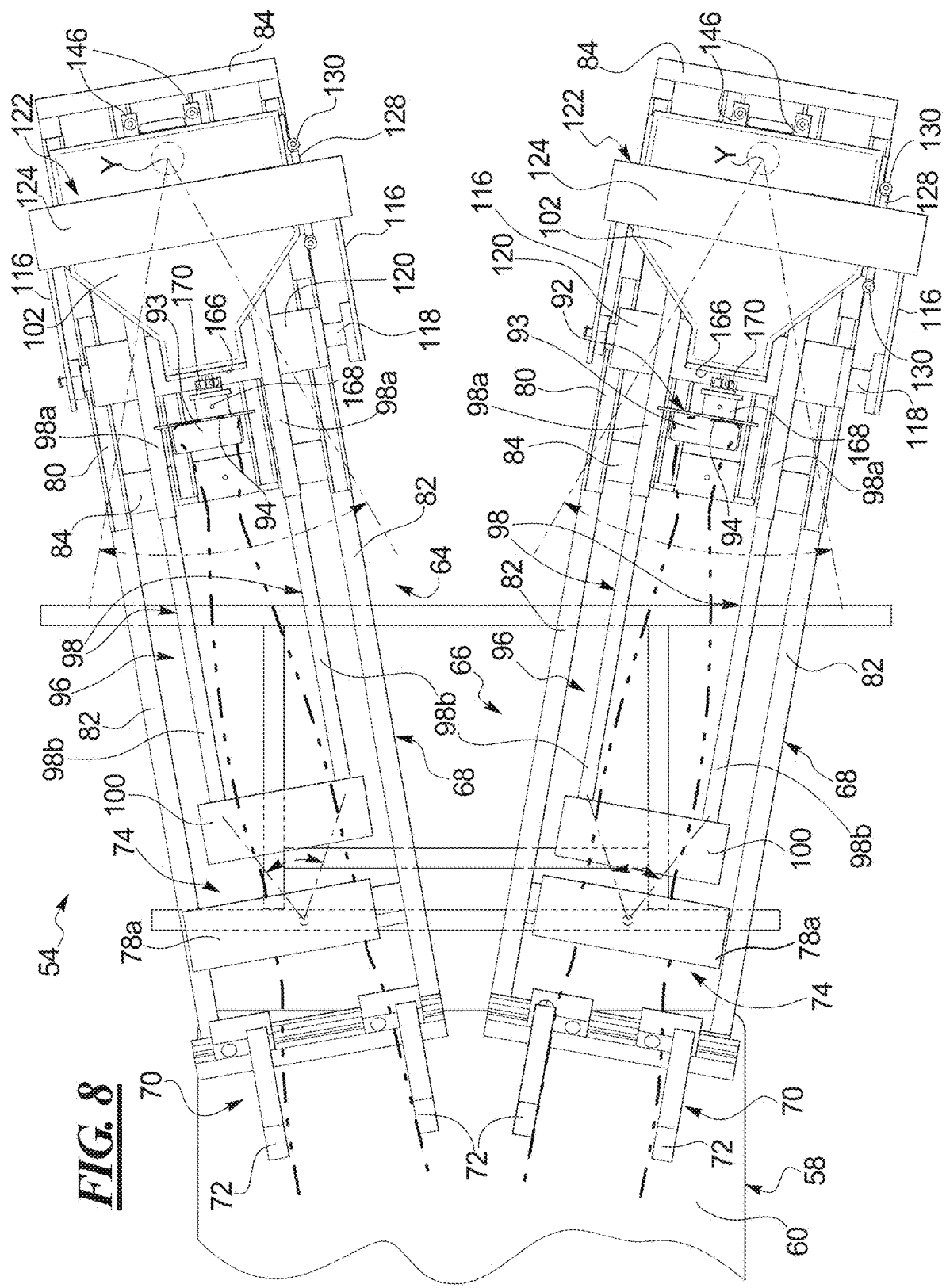
FIG. 8 shows a top view of the robot of FIG. 5 and illustrates Varus-valgus motion of the robot about the Y-axis of each of the left and right leg portions of the robot.

As represented in FIG. 8, the Y-axis drive 106 is configured to conduct a Varus-valgus or V-V test on a patient's knee. Position sensors can be applied to appropriate locations on the right leg of the patient. The Y-axis drive 106 imparts force about the Y-axis to initiate Varus-valgus motion in the tibia part of the knee joint relative to the fixed femur part of the knee joint of the patient, as shown in FIG. 8. The motor 140 can reversibly rotate the output shaft 144 through an arc about the Y-axis whereby the pivot plate 150 is rotated through the same arc. This in turn moves, i.e., pivots the Z-axis drive 108 side-to-side, which in turn pivots the foot plate 92 and the tibia rods 98 about the Y-axis. Movement of the tibia rods 98 moves the patient's lower leg side-to-side relative to the femur. The Y-axis torque transducer 148 measures the applied torque at the output shaft 144 caused by the load applied at the calf plate 100 or along the tibia rods as the tibia rods push the patient's tibia medially or laterally relative to the femur. Motion and load data can be collected by a processor from the sensors relative to the motion in the patient's leg and from the Y-axis torque transducer 148 relative to the torque or applied forces.

The motor 140 and/or gearbox 142 can be designed to produce a limited range of travel, which may be substantially less than 360 degrees of rotations, in the output shaft 114. In addition or in the alternative, the Y-axis drive 108 components can also be designed to incorporate a mechanical travel limiter, if desired, though not shown or described herein.

The above-described Varus-valgus movement components of the tibia positioning assembly 90 can also vary considerably from the example shown and described herein. The sled assembly 86, motor mounts 146, pivot plate 150, and support brackets 154 can be eliminated or can take on different positions, configurations, and constructions. For example, the pivot plate 150 can include a curved guide slot 156 formed through the plate, as shown in FIG. 4. The guide slot 156 can be spaced a radial distance from the Y-axis and the output shaft 144 of the motor 140. A guide post 158 can be fixed to the sled assembly 86 and project upward toward the guide slot 156. A tip 159 of the guide post 158 can be captured in or seated in the guide slot and can be configured to both support the pivot plate 150 thereat and to slide along the guide slot as the pivot plate is rotated by the motor 140. Likewise, the configuration and construction of the cross-plate 120, tibia rods 98, calf plate 100, shell 102, and the like can also be varied. The mechanisms or devices that are used to secure a patient's leg to the tibia rods 98 and to the foot plate 92, if and when needed for testing, can also vary.

As shown in FIGS. 4 and 6, the Z-axis drive 108 can also include a third motor, which can also be an electric motor 160, a gearbox 162, and an output shaft 144 that is driven by the motor and gearbox. The gearbox 162 and motor 160 are fixed to a motor mounting bracket 166 that is attached to a front end of the pivot plate 150 and forward of the X-axis drive 104. In this example, the Z-axis is aligned with both the X-axis and the Y-axis, though in other examples this might not be the case. The entire Z-axis drive, including the foot plate 92, can also slide lengthwise along the sub-frame 68 to adjust the foot plate 92 position relative to the table assembly 52 and/or the thigh and knee stabilizers 70, 74 as noted above. A Z-axis torque transducer 168 is fixed to the output shaft 164 by an adaptor 170 for rotation therewith. In this example, the motor 160 and gearbox 162 are positioned behind the motor mounting bracket 166 and the adaptor 170 and torque transducer 168 are disposed forward of the mounting bracket. The enclosure defined by the shell 102 and the pivot plate 150 house the Z-axis drive 108, other than the foot plate 92, as noted above. The foot plate 92 is secured to the torque transducer 168 for rotation therewith. Thus, as the output shaft 164 is reversibly rotated by the motor 160 and gearbox 162 about the Z-axis, as shown in FIG. 9, the foot plate 92 will all rotate about the Z-axis.

Figure 9:
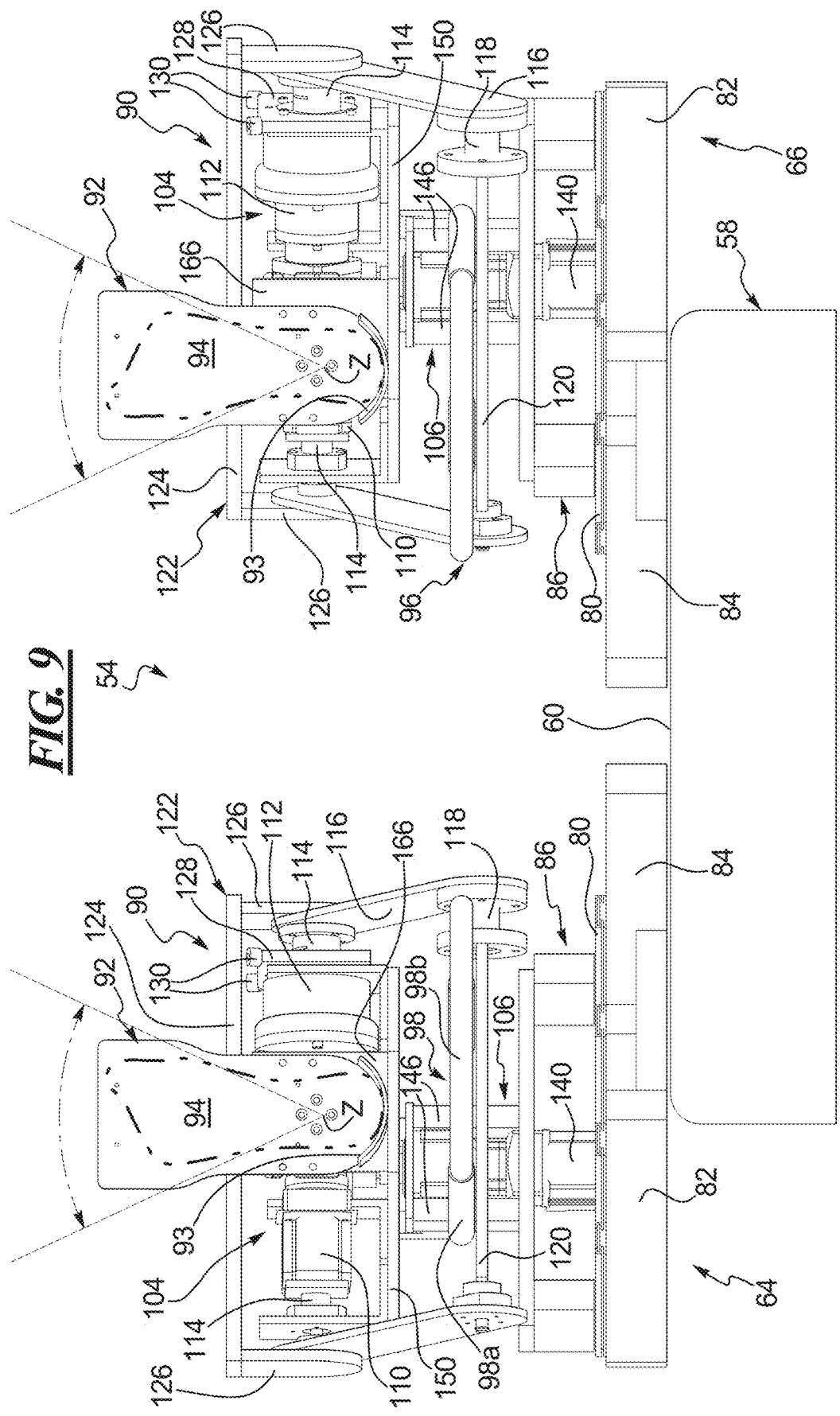
FIG. 9 shows an end view of the robot of FIG. 5 from the point of view and in the direction of the arrow IX and illustrates internal and external rotation of the robot about the Z-axis of each of the left and right leg portions of the robot.

As represented in FIG. 9, the Z-axis drive 108 is configured to conduct an internal and external rotation or simply a tibia rotation test on a patient's knee. Position sensors can be applied to appropriate locations on the right leg of the patient. The Z-axis drive 108 imparts force about the Z-axis to initiate rotation motion in the tibia part of the knee joint relative to the fixed femur part of the knee joint of the patient, as shown in FIG. 9. The motor 160 can reversibly rotate the output shaft 164 through an arc about the Z-axis whereby the adapter 170 and torque transducer 168 are rotated through the same arc. This in turn moves, i.e., rotates the foot plate 92 about the Z-axis. Movement of the foot plate 92 in this manner rotates the patient's lower leg internally and externally relative to the femur. The Z-axis torque transducer 168 measures the applied torque at the output shaft 164 caused by the load applied at the foot plate 92 as the foot plate rotates the patient's tibia or lower leg internally and externally relative to the femur. Motion and load data can be collected by a processor from the sensors relative to the motion in the patient's leg and from the Z-axis torque transducer 168 relative to the torque or applied forces.

The motor 160 and/or gearbox 162 can be designed to produce a limited range of travel, which may be substantially less than 360 degrees of rotations, in the output shaft 164. In addition or in the alternative, the Z-axis drive 108 components can also be designed to incorporate a mechanical travel limiter, if desired. A simple mechanical stop can be positioned to stop movement of the foot plate 92 in either rotation direction, if desired. Such a sop can be the tibia rods 98 or something mounted thereto. Alternatively, such a stop can be applied to the motor mounting bracket 166 or the like.

The above-described rotation movement components of the tibia positioning assembly 90 can also vary considerably from the example shown and described herein. The foot plate 92 and motor mounting bracket 166 can be eliminated or can take on different positions, configurations, and constructions. The mechanisms or devices that are used to secure a patient's leg to the foot plate 92, if and when needed for testing, can also vary.

The above described motors, gearboxes, and output shafts can also vary within the scope of the disclosure. The motors can be servo-motors or other types of motors suitable for precise motion and torque control and for the loads to which the motors will be exposed during such limb testing and evaluation. Any of the first, second, or third, i.e., X-, Y-, or Z-axis, drives with respect to the motors and gearboxes can be structurally configured substantially the same relative to one another, with the only substantive difference being the relative axis of rotation about which each is oriented. Alternatively, each drive can incorporate a motor and/or gearbox that is different than one or both of the others as well. The torque transducers can be selected in order to provide torque readings as known in the art relating to each of the three drives. In other examples, one or more of the torque transducers may be replaced with other torque or load sensors or load sensing means. For example, motor current may be measured to determine the torque or load on the motor output shaft during use. Any suitable means for modeling torque may be used. The torque readings can be calibrated and calculated as needed to correspond to known torque or force values imparted to a patient's limb(s). Movement of the patient's body parts may be detected by non-invasive systems, as noted above, that utilize sensors or markers that are attached to the skin, including but not limited to vision, optoelectronic, ultrasonic, and electromagnetic motion analysis systems.

In use, a patient lies on the padded surface 60 of the platform 58 on the table assembly 52 as shown in FIG. 5. The patient's knees are positioned to engage the knee stabilizers 74, their thighs are positioned to engage the thigh stabilizers 70, their feet are positioned to engage the foot plates 92, and their calves are positioned to engage the tibia rods. The patient can then be secured to the foot plates, to the knee stabilizers, and to the thigh stabilizers for testing and evaluation. The patient's calves or tibias can also be secured to the tibia rods 98, as needed for specific testing. Movement of the lower leg of the patient may be detected by non-invasive systems utilizes sensors or markers that are attached to the skin, including but not limited to optoelectronic, ultrasonic, and electromagnetic motion analysis systems. In one example, the RKT apparatus can be configured so that the patient's knees are flexed to about 30 degrees between the femur and the tibia. However, the tests or evaluations may also include the additional capability to flex the knee from 0 to 90 degrees to allow for similar tests (such as the examples above) done for different degrees of knee flexion.

Any one of the X-, Y-, and Z-drives can be decoupled from any of the other two. In the disclosed example, each of the three drive assemblies may be operable with one or more of the other at the same time or can be decoupled from each of the other two and be operable independent of the other two. In other examples, two or more, and perhaps all three of the drives can be mutually coupled relative to one another such that movements are substantially simultaneously imposed upon the patient's legs during use of the RKT apparatus. The combined simultaneous operation of two or all three of the motors allows the RKT apparatus to perform more complex testing, such as simulating the known manual pivot shift testing procedure.

The aforementioned sensors can be provided on the legs of a patient, in the power lines of the RKT apparatus, and/or on the X-, Y-, and Z drives to obtain desired position or location data as the lower leg is moved during testing and evaluation. The degree of movement of the patient's legs in the A-P test, the V-V test, and/or the rotation test can be measured by detecting the movements of the parts of the apparatus, the rotation of the drives, and/or the actual movements of the patient's legs. The torque encountered during each test and over the range of motion applied during each such movement may also be measured, suitably calibrated to the limb movement, and recorded. Various X-, Y-, and Z-axes can also be determined and recorded for and/or relating to the femoral and tibial axis of the patient for testing.

Figure 10:
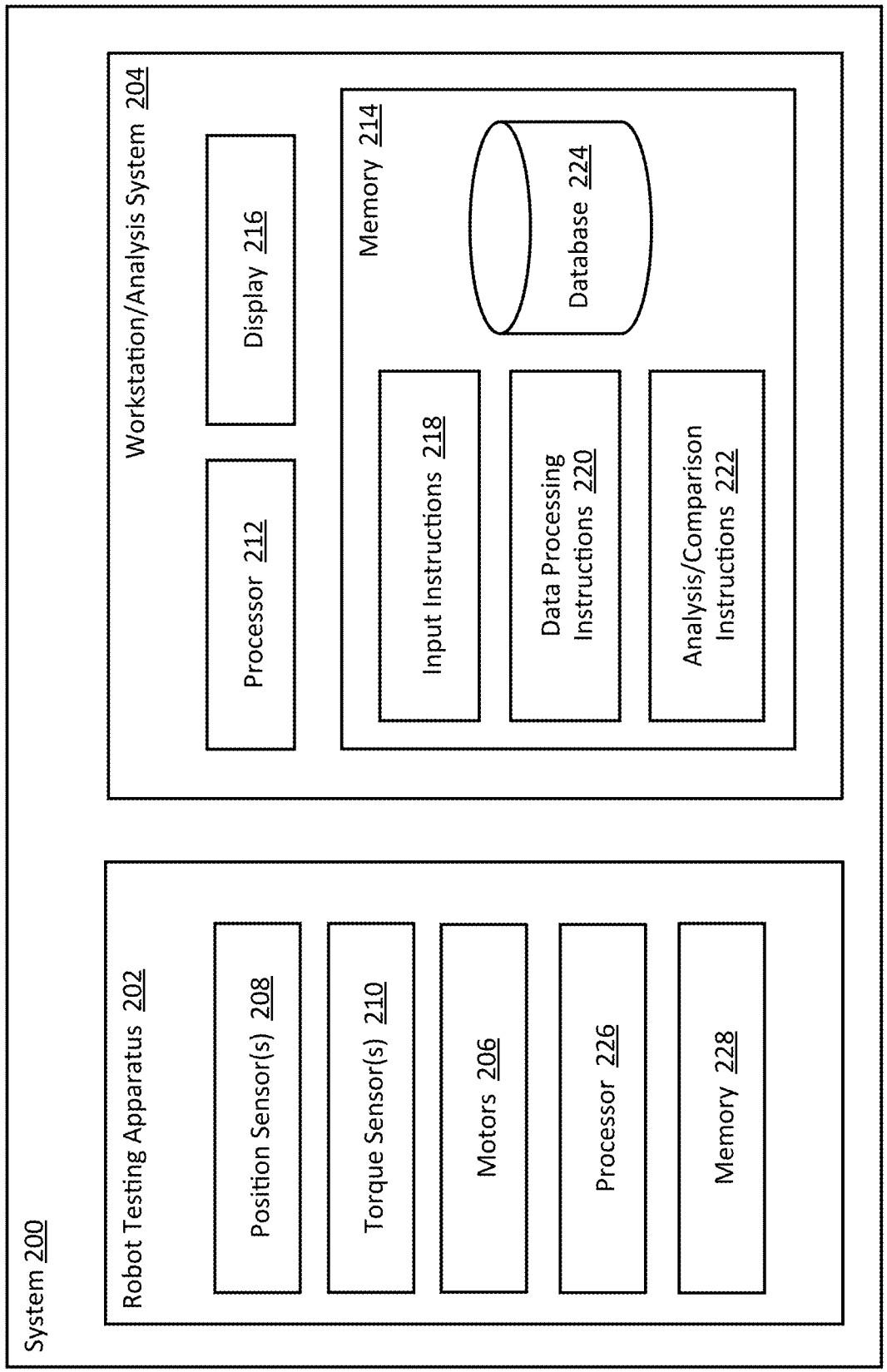
FIG. 10 is a block diagram of a system for characterization and analysis of joints involving multiple independent tests in accordance with one example.

FIG. 10 illustrates a system 200 directed to determining a condition of a joint based on analysis of primary and secondary joint test data. In this example, the system 200 includes a robot testing apparatus 202 and an analysis system 204 in communication with the robot testing apparatus 202. The analysis system 204 may be a workstation or other computer coupled to the robot testing apparatus 202. In this example, the communications and coupling between the robot testing apparatus 202 and the analysis system 204 are directed to providing data acquired by the robot testing apparatus 202 to the analysis system 204. Alternatively or additionally, the communications are directed to allowing the analysis system 204 to control one or more aspects or features of the robot testing apparatus 202.

The robot testing apparatus 202 is configured to implement joint testing, such as rotational joint testing and translational joint testing of a joint. The robot testing apparatus 202 implements the rotational and translational joint testing to acquire or capture test data indicative of rotational and translational movement of the joint during the rotational and translational joint testing, respectively. For instance, in implementing such testing, the robot testing apparatus 202 may be configured to detect position and force (e.g., torque) data while a force (e.g., torque) is applied to the joint. The position data may be processed to determine translational displacements along three orthogonal axes of a coordinate system that define or correspond with three degrees of freedom for the joint, as well as orientations (e.g., rotational displacements) about those three axes that correspond with the other three degrees of freedom for the joint. A range of rotational or translational motion may then be determined for the joint in each degree of freedom. Other types of data indicative of the rotational and translational movement of the joint during the rotational and translational joint testing may be acquired. For instance, the rotational and translational position data acquired by the robot testing apparatus 202 may be analyzed in combination with the force (e.g., torque) level(s) applied or created during the testing, as described below.

The robot testing apparatus 202 includes a number of motors 206, one or more position sensors 208 directed to capturing position data, and one or more torque sensors 210 directed to capturing torque data. The motors 206, the position sensor(s) 208, and the torque sensor(s) 210 may be otherwise configured as described above in connection with FIGS. 1-9. For instance, as described above, each torque sensor 210 may be an integrated torque transducer of a respective one of the motors 206. The torque sensors 210 may be used to detect the torque applied by the respective motor 206 or measure a reactive force resulting from the application of the torque.

The robot testing apparatus 202 implements the joint testing by imparting or applying one or more forces to the joint. The motors 206 of the robot testing apparatus 202 are configured such that each force is oriented in a respective plane or degree of freedom for the joint. The degree of freedom is disposed within the respective plane. In examples in which the joint is a knee, the joint testing may include a respective torque applied to cause external-internal rotational movement and/or varus-valgus rotational movement. In the examples described above, the external-internal rotational movement is implemented by the motor 206 corresponding with a Z-axis drive. The motor 206 for the Z-axis drive causes rotation about the Z-axis within a plane that corresponds with the X-Y plane. The varus-valgus rotational movement is implemented by the motor 206 for a Y-axis drive that causes rotation about the Y-axis within a plane that corresponds with the X-Z plane. The joint testing may alternatively or additionally include a force applied to cause anterior-posterior translational movement. As described above, the anterior-posterior translational movement may be driven by the motor 206 for an X-drive that causes movement (rotation and/or translation) within a plane that corresponds with the Y-Z plane. Additional and/or alternative joint tests may be implemented. Multiple, different types of tests may be useful in situations in which a joint abnormality is revealed in connection with a subset (e.g., one) of the testing planes or degrees of freedom, but not in other planes or degrees of freedom. The number and types of the joint tests implemented by the robot testing apparatus 202 may thus vary accordingly.

The joint tests and testing planes are associated with respective degrees of freedom for the joint. Each joint test imparts force oriented in a respective degree of freedom for the joint. The movement in the degree of freedom in which the force or torque is applied or imparted may be referred to as the primary movement for the joint test. A test may have multiple applied forces and, accordingly, multiple primary movements. The movement in the degrees of freedom in which a force is not applied or imparted may then be referred to as secondary or concomitant movement for the joint test. The concomitant movement arises from the imparted force due to the nature or condition of the joint, even though the underlying force is not oriented in the degree of freedom of the concomitant movement.

The robotic testing apparatus 202 is configured to capture data indicative of the motion of the joint during the joint testing. The data may be raw sensor data generated by the position sensors 208 and the torque sensors 210 and/or processed data derived from the raw data. Either way, to acquire the data, the robotic testing apparatus 202 may apply a range of forces (e.g., torque levels) to the joint under test. The sensors 208, 201 capture the position and torque data during the resulting joint movement. For example, the position and torque data from each sensor 208, 210 may be sampled at a particular rate. The position and torque data may then be processed (e.g., interpolated) to generate test data at specific intervals, such as specific torque levels.

The torque sensors 210 may provide torque data regardless of whether the motor 206 with which the torque sensor 210 is associated is applying force to the joint. The torque sensor 210 for an inactive one of the motors 206 may thus provide data indicative of the reactive force resulting from the torque applied in another plane or degree of freedom. The reactive force is indicative of the force applied by the joint on the torque sensor 210 of the inactive motor 206. The measured reactive forces may thus be referred to as secondary, concomitant, or incidental forces or torques.

The processing of the raw data may include generating data indicative of an extent, displacement, or range of motion in one or more degrees of freedom for the joint. For instance, the respective extent or range of motion may be determined for the primary movement and/or one or more secondary movements resulting from the application of a range of force (e.g., torque) levels.

The processing of the raw data may also include combining the position and force (or torque) data to generate load-deformation data for the joint under test. The load-deformation data for the joint may include a set of force-position data points over the range of forces. The load data in each data set may be representative of the applied force (or torque) or the resulting reactive force (or torque) measured in one of the other degrees of freedom.

Figure 12:
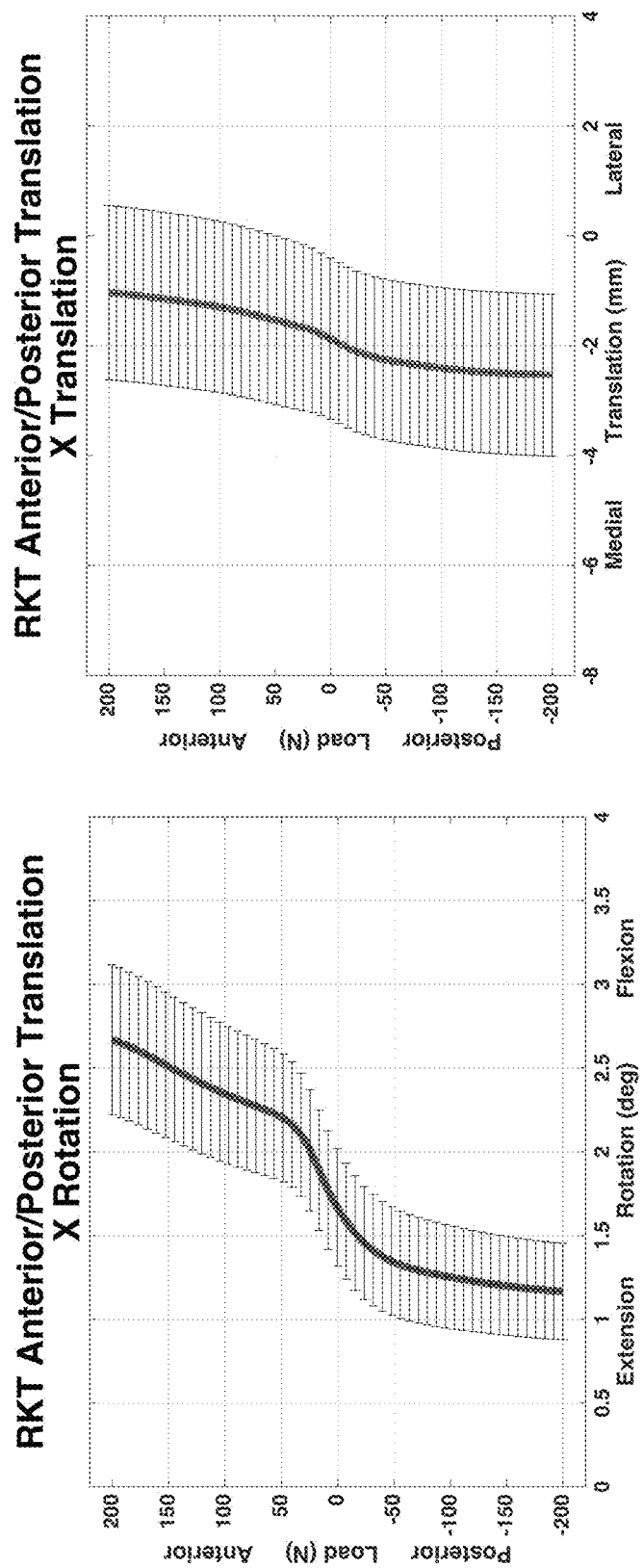
FIGS. 12-14 are examples of load-deformation curves indicative of load-deformation curve data generated by the system of FIG. 10 or the method of FIG. 11.
Figure 13:
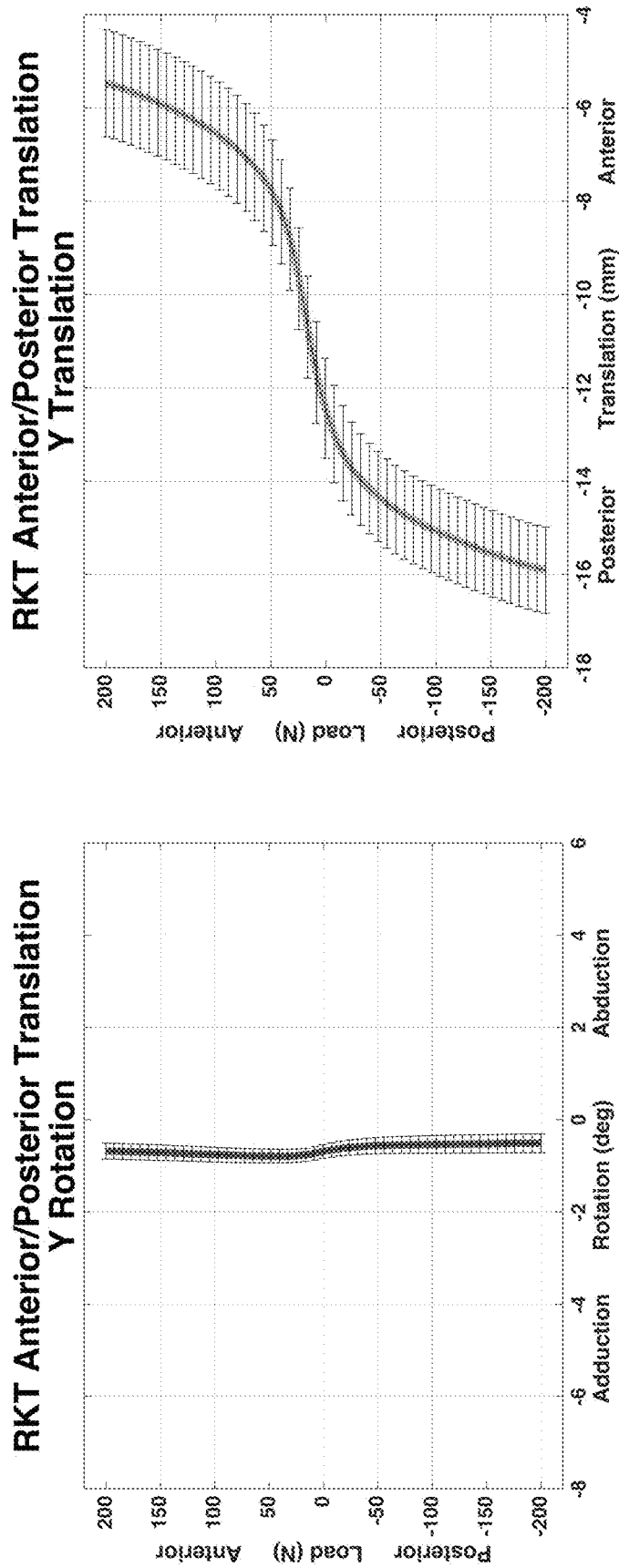
Figure 14:
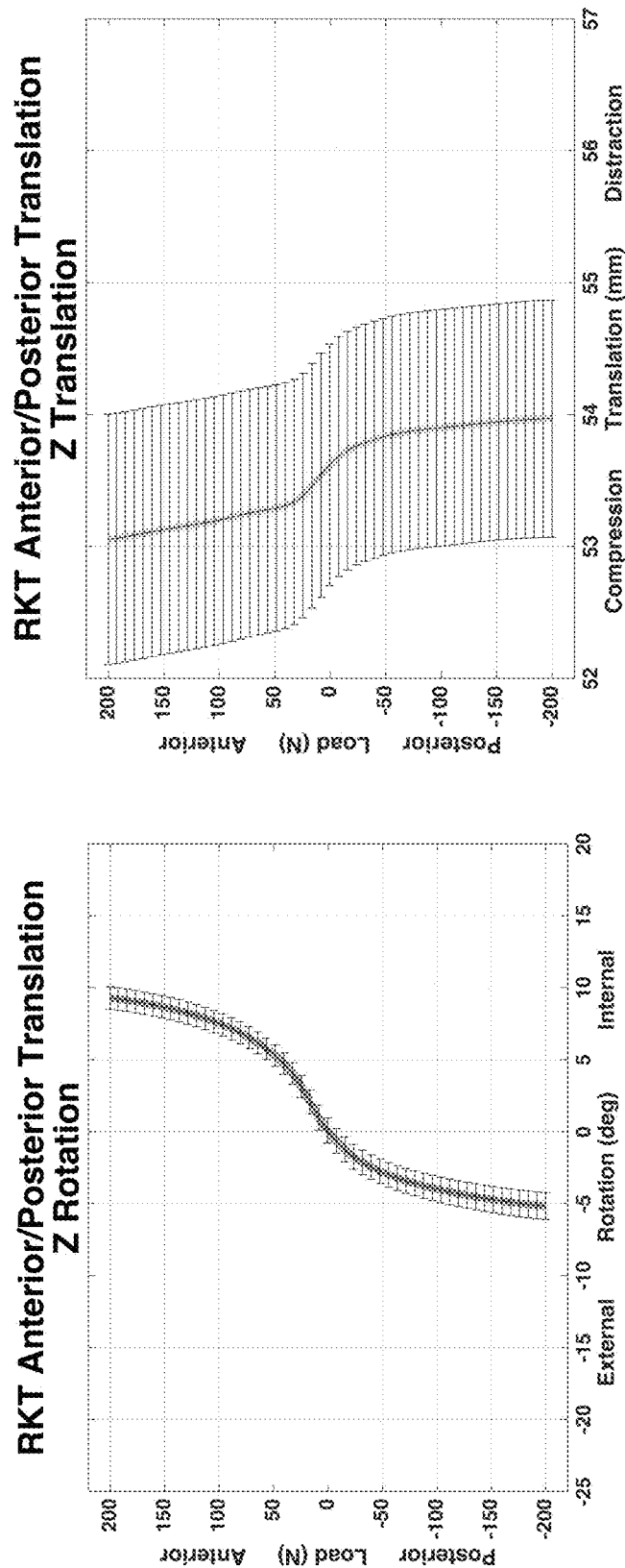

Example load-deformation plots are shown in FIGS. 12-14 for an anterior-posterior translation test of a knee joint. A respective load-deformation plot is provided for each degree of freedom. In an anterior-posterior translation test, the primary movement is the Y-translation shown in FIG. 13. The other load-deformation plots present test data indicative of the concomitant movement of the knee joint during the test in the other five degrees of freedom. In this example, the position data for the concomitant movement in each one of the other degrees of freedom is plotted against the applied force. That is, the force data is provided by the torque sensor 210 for the motor 206 that applies the force, i.e., the motor 206 associated with the X-drive in this case.

Each load-deformation plot in FIGS. 12-14 includes a load-deformation curve fitted to the load-deformation data points for the respective degree of freedom. The underlying load-deformation data points are not shown for ease in illustration. The uncertainty in the curve fitting is shown via bars at respective force levels.

In other cases, the data provided by the other torque sensors 210 (i.e., other than the torque sensor 210 that measures the applied force) may be used to generate load-deformation data. That is, the position data for the concomitant movement is plotted against the resulting force measured in one of the other degrees of freedom, such as the degree of freedom for the position data. For example, the Z-axis rotation position data gathered during an anterior-posterior test may be plotted against the reactive force measured by the torque sensor 210 for the motor 206 associated with the Z-drive (rather than the applied force as shown in FIG. 14). More generally, the position data for any one of the six degrees of freedom may be combined with the torque or force data measured by any one of the torque sensors 210.

The analysis system 204 includes a processor 212 and a memory 214 for processing the load-deformation data captured by the robot testing apparatus 202. The processor 212 is coupled to, or otherwise in communication with, the robot testing apparatus 202. In this example, the analysis system 204 also includes a display 216 for providing a user interface for an operator of the analysis system 204. The user interface may be directed to controlling the robot testing apparatus 202 and/or the analysis system 204. The user interface may be alternatively or additionally directed to presenting the results of the processing.

The processor 212 is coupled to the memory 214 to access instructions and/or other data stored on the memory 214. In the example of FIG. 10, input instructions 218, data processing instructions 220, and analysis instructions 222 are stored on the memory 214. The instructions 218, 220, 222 may be stored as one or more modules or instruction sets, and may be integrated to any desired extent. The memory 214 may have additional data stored thereon, such as load-deformation data for the joint under test or other joint instances. The memory 214 may be or include any number of storage devices, memories, and/or other computer-readable media.

The processor 212 is configured through execution of the input instructions 218 to obtain test data for a joint. As described above, the test data is indicative of motion of the joint during the joint testing implemented by the robotic testing apparatus 202. The test data may be obtained by conducting one or more joint tests. During each test, the robotic testing apparatus 202 is applied to the joint to impart force(s) oriented in one or more planes or primary degrees of freedom for the joint. Multiple concurrent motions in multiple degrees of motion may thus be concurrently driven. Raw sensor data may be obtained for one or more tests. In some cases, the input instructions 218 cause the processor 212 to request the test data from the robot testing apparatus 202. In other cases, the data may be received (e.g., provided) without a request. For instance the input instructions 218 may cause the processor 212 to access the memory 214 to obtain the test data, e.g., from previously implemented joint testing.

The test data may thus be obtained in additional and/or alternative ways. For instance, the processor 212 may be configured to obtain the underlying raw sensor data from the robot testing apparatus 202 for the joint testing. In some cases, the test data obtained from the robot testing apparatus 202 may be or include processed data.

In some cases, the input instructions 218 (and/or other instructions) cause the processor 212 to process the data provided by the robot testing apparatus 202. The data processing may be directed to preparing the data for calculations directed to expressing the motion in one or more planes or degrees of freedom. For example, the processing may include one or more coordinate system transformations and/or other kinematic processing. In some knee joint examples, the transformations include transforming (1) the femur orientation from an anatomical space (defined, e.g., via anatomical markers) to a world coordinate system of the robot testing apparatus 202, (2) the tibia orientation from an anatomical space to the world coordinate system, (3) the femur orientation from the world coordinate system to a sensor coordinate system (e.g., a femur or tibia sensor), (4) the tibia orientation from the world coordinate system to a sensor coordinate system, and (5) the tibia orientation from the world coordinate system to a femur coordinate system. Further transformations may be used to account for the origins of the coordinate systems. Collectively, these transformations may be directed to producing data indicative of the motion of the joint from a particular perspective. For instance, in some knee joint examples, the data is indicative of the motion of the tibia in the coordinate system of the femur. The extent to, and manner in, which the sensor data provided to the processor 212 is processed via the input instructions 218 may vary. For instance, the sensor data may be normalized or interpolated to any desired extent. Further details regarding examples of the coordinate systems are set forth in one or more of the above-referenced co-pending applications.

The processor 212 is configured through execution of the data processing instructions 220 to generate data indicative of movement of the joint in the primary and secondary degrees of freedom based on the test data. Movement data for each primary degree of freedom may be generated from (e.g., as a function of) the test data. The primary degree(s) of freedom correspond with the degree(s) of freedom in which motion is driven during the joint test. Such primary movement data may be or include the extent or range of motion or other displacement in the respective primary degree of freedom. Alternatively or additionally, the primary movement data is or includes load-deformation data for the primary motion. The load-deformation data combines the position data for the primary degree of freedom with the data indicative of the applied force.

Movement data may be generated for one or more of the other, or secondary, degrees of freedom based on the test data. Such secondary movement data is indicative of concomitant movement of the joint in any one of the degrees of freedom for the joint other than the primary degree(s) of freedom. As described above, the concomitant movement arises from the imparted force applied in the primary degree(s) of freedom. Together, the primary and secondary degrees of freedom correspond with two or more of the six degrees of freedom in which the robotic testing apparatus 202 allows a bone of the joint to move during testing.

The secondary movement data may be or include the extent or range of motion or other displacement in the respective secondary degree of freedom. Alternatively or additionally, the secondary movement data is or includes load-deformation data for the secondary motion. The load-deformation data combines the position data for the secondary degree of freedom with the data indicative of the applied force and/or the resulting (e.g., reactive) force. The secondary movement data may include alternative or still further information, including, for instance, one or more derivatives of the load-deformation curve(s) and/or other curves, such as the derivative of the secondary movement with respect to the primary movement.

The implementation of the data processing instructions 220 in connection with knee joint examples may involve processing the test data from an anterior-posterior translation test, an external-internal rotation test, a varus-valgus test, or a test involving a combination of the motion in such tests. In the example shown in FIGS. 12-14, the test data is processed for an anterior-posterior translation test. In that case, the primary degree of freedom (or movement) is translation along the Y-axis. The secondary degree(s) of freedom (or movement) may be y-axis rotation (FIG. 13), X-axis rotation and X-axis rotation (FIG. 12), and Z-axis rotation and Z-axis translation (FIG. 14).

The load-deformation data for a particular degree of freedom may be or include a load-deformation curve fitted to the load-deformation data. A variety of different curve fitting techniques or procedures may be used to generate a load-deformation curve for the load-deformation data. For instance, any of the curve techniques used in connection with functional data analysis may be used. In some examples, regression modeling techniques, principal component analysis (PCA), or other techniques are used. In other cases, one or more quadratic curves are fitted to the load-deformation data. Other polynomial functions of varying order may alternatively be used. Further details regarding examples of curve fitting procedures and generation of the load-deformation data are set forth in one or more of the above-referenced patent applications.

In some cases, the data processing instructions 220 process the test data for a further test that imparts force oriented in one of the previously secondary degrees of freedom. For example, the further test may be internal-external rotation, which involves rotation about the Z-axis. Rotation about the Z-axis was a secondary degree of freedom for the previous test (anterior-posterior translation), but is now the primary degree of freedom for the current test. The data processing instructions 220 may then generate data indicative of the primary and secondary movement occurring during the internal-external rotation test. Alternatively or additionally, the data processing instructions 220 may generate the primary and secondary movement data for test data collected during a test that involves concurrent movement in the degrees of freedom associated with anterior-posterior translation and internal-external rotation.

Data indicative of the primary and secondary movement may be stored in the memory 214 and/or another data store. In the example of FIG. 10, the primary and secondary movement data is stored in a database 224. The primary and secondary movement data may be stored as respective sets of data points and/or a set of parameters of curve function data, such as polynomial coefficient, PCA factor levels, or other factors generated by a fitting procedure.

The processor 212 is configured through execution of the analysis instructions 222 to determine a condition of the joint based on an analysis of the primary movement data and the secondary movement data for the joint test(s). As described above, the primary movement data may include multiple data parameters, sets, or other elements. The multiplicity of data elements may arise from multiple joint tests for a given joint and/or multiple applied forces during a respective joint test. The secondary movement data may also include multiple data parameters, sets, or other elements. The multiplicity of data elements may likewise arise from multiple joint tests and multiple applied forces during a respective joint test, as well as from data being generated for multiple secondary degrees of freedom or concomitant movements during a given joint test. Any of these data elements may be analyzed via implementation of the analysis instructions 222.

The analysis of the primary and secondary movement data may vary in accordance with the nature of the primary and secondary movement data. For instance, when the primary and secondary movement data is an extent or range of motion, the analysis may be or include a comparison with a respective threshold. A respective threshold may be provided for each primary degree of freedom as well as one or more secondary degrees of freedom. In a knee joint example involving an anterior-posterior translation test, a threshold range is provided for comparison with the Y-axis translation movement data, and one or more threshold ranges are provided for comparison with the Y-axis rotation movement data, the X-axis translation and rotation data, and/or the Z-axis translation and rotation data. Any comparison involving a threshold may alternatively or additionally involve a comparison with multiple thresholds, a distribution, and/or other data.

In cases in which the primary and secondary movement data includes load-deformation curve data, the analysis instructions 222 (and/or the data processing instructions 220) may cause the processor 212 to identify one or more characteristics of the load-deformation data for the primary and secondary movement data. For instance, the load-deformation curves of FIGS. 12-14 are indicative of the primary and secondary movement observed during the Anterior/Posterior Drawer clinical test of a healthy or normal knee joint. Examples of characteristics include the location of the equilibrium of the knee joint in connection with one or more of the degrees of freedom. All of the tibial position data points depicted therein are referenced to the femoral coordinate system, as described above. With that in mind, the zero torque levels in the translation plots of FIGS. 12, 13, and 14 show that the tibial origin at equilibrium sits medial, posterior, and distal to the femoral origin, respectively. Turning to the rotation plots of FIGS. 12, 13, and 14, the tibial coordinate system at equilibrium sits slightly flexed, adducted, and externally rotated relative to the femoral coordinate system. Further details regarding examples of joint equilibrium position determinations are set forth in one or more of the above-referenced patent applications. These and other characteristics, when viewed in various combinations, may be associated with respective joint conditions, e.g., abnormalities.

Alternatively or additionally, the analysis instructions 222 (and/or the data processing instructions 220) may cause the processor 212 to quantify a feature of the load-deformation curves for the primary and secondary movement data. For instance, the analysis may include comparing derivative data for the load-deformation curves for the primary and secondary degrees of freedom with thresholds. For instance, the derivative data may be or include the first and/or second derivative of the load-deformation curve. These and other derivatives may be quantified at various points along the curve, such as at the endpoint(s), at zero torque, or at any other torque level. A higher or steeper slope represents a less compliant or stiffer joint, whereas a lower slope represents a more compliant or looser joint. Additional, alternative, or fewer comparisons involving the load-deformation data may be implemented. For instance, the width of the hysteresis exhibited by the load-deformation curve (e.g., at a zero torque level) may be compared or otherwise analyzed. In other cases, the shape of the curve may be quantified in various ways. For instance, a quantitative representation of the roundness (or other shape parameter) may be a useful feature comparison. A particular curve shape may be associated with a respective type of injury or other abnormality. The association may depend on the presence or absence of other features, as addressed below in connection with the compilation of a profile for the joint under test.

The feature may also be one of the defining parameters of the curve function. In PCA examples, the feature may be quantified by extracting one of the PCA factor levels. In other cases, various types of coefficients may also be extracted for analysis.

For the quantified feature(s) of the load-deformation curves for the primary and secondary movement data, the curve analysis instructions 222 may cause the processor 212 to implement a comparison of the quantified feature(s) of the load-deformation curves with preset load-deformation data to identify a condition (e.g., a biomechanical characteristic) of the joint. The preset load-deformation data may be associated with a plurality of joint instances. The preset load-deformation data for the joint instances may have been generated using the same testing apparatus (or type of testing apparatus) used to acquire the load-deformation data for the joint under test. In that way, the patient set-up and other factors underlying the data acquisition are consistent across the joint instances. In the example of FIG. 10, the preset load-deformation data is stored in the database 224. Other data storage devices may be alternatively or additionally be used.

In some cases, the analysis may include implementation of a pattern detection procedure. For instance, the pattern detection procedure may be directed to analyzing the quantified feature(s) of the load-deformation curves to determine whether the shapes of the curves match predetermined curve shapes. A set of detected patterns in the primary and secondary movement data may be indicative of healthy or injured joints.

In some cases, the analysis of the primary movement data and/or the secondary movement data involves multiple comparisons. For example, multiple curve features may be quantified for one or more of the degrees of freedom being analyzed. Non-curve features may also be compared or analyzed in conjunction with the curve feature(s). A profile for the joint under test may thus be compiled, the profile including both curve and non-curve features in some cases. The profile may then be compared against other profiles of abnormal and/or normal joints. The other profiles may be stored as preset data (e.g., preset profile data) in the database 224. The preset data may be updated as new profile data is gathered and analyzed. The new profile data may then be associated with a confirmed diagnosis or other assessment of the joint condition. Data indicative of the assessment may thus be added to the profile for the joint. The performance of the analysis system 204 may thus be improved over time via the integration of new profile data into the database 224.

A variety of non-curve feature data may be included in the profiles. For example, the profile may include height, weight, and other data indicative of the subject. The computed joint play quantity may also be incorporated into the profile. Any data that may be helpful to identifying a joint abnormality may be incorporated. For example, the profile data may specify data indicative of the bones that define the joint under test, such as structural characteristics of the bones, the three-dimensional surfaces of the bones, and the contact points between the bones. Any of these or other parameters may be involved in the analysis (e.g., comparison with the profile data) of the profile of the joint under test implemented via the analysis instructions 222.

The curve analysis instructions 222 may then configure the processor 212 to assess the profile to identify an abnormality of the joint under test. The assessment may include comparing the profile with the profile data to find one or more matches or closest matches. A profile match may identify multiple abnormalities.

Various combinations of the profile and other comparisons may be used. In these ways, the load-deformation curves and other primary and secondary movement data may support a variety of different analyses of the movement of the joint under test. Any number of features of the load-deformation curves or other primary and secondary movement data may be extracted or otherwise selected for comparison with the preset data and/or other analysis. The comparison or other analysis may be directed to identifying one or more characteristics of the joint. One or more characteristics or conditions of the joint under test may then be identified by matching the joint under test with other joints having similar data.

The analysis system 204 and the robot testing apparatus 202 may be integrated with one another to any desired extent. In the example of FIG. 10, the robot testing apparatus 202 includes a processor 226 and a memory 228. The processor 226 and the memory 228 may be dedicated to supporting the data acquisition and communication functions of the robot testing apparatus 202. For instance, the processor 226 and the memory 228 may not be configured to implement the quantification and evaluation aspects of the system 200. In other cases, the processor 226 and the memory 228 are involved in the execution of the input instructions 218, the curve function generation instructions 220, and the curve analysis instructions 222. In still other cases, the robot testing apparatus 202 and the analysis system 204 share one or more processing and/or memory components.

Each processor 212, 226 may be or include any number or type of processing cores, processors, processing units (e.g., a central processing unit or graphical processing unit), or processing systems. Each processor 212, 226 may be a component in a variety of systems. For example, each processor 212, 226 may be part of a standard personal computer or a workstation. Each processor 212, 226 may be or include one or more general processors, digital signal processors, application specific integrated circuits, field programmable gate arrays, servers, networks, digital circuits, analog circuits, combinations thereof, or other now known or later developed devices for analyzing and processing data.

Each memory 214, 228 may be or include any number or type of computer-readable memories, media, or other devices on which data is stored. Each memory 214, 228 may be or include a main memory, a static memory, or a dynamic memory. Each memory 214, 228 may include, but may not be limited to computer readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In one case, each memory 214, 228 may include a cache or random access memory for a processor. Alternatively or additionally, each memory 214, 228 may be separate from the processor, such as a cache memory of a processor, the system memory, or other memory. Each memory 214, 228 may be or include an external storage device or database for storing data. Examples may include a hard drive, compact disc ("CD"), digital video disc ("DVD"), memory card, memory stick, floppy disc, universal serial bus ("USB") memory device, or any other device operative to store data. Each memory 212, 228 may be operable to store instructions executable by a processor. The functions, acts or tasks illustrated in the figures or described herein may be performed by the programmed processor executing the instructions stored in the memory 214, 228. The functions, acts or tasks may be independent of the particular type of instruction set, storage media, processor or processing strategy and may be performed by software, hardware, integrated circuits, firmware, micro-code and the like, operating alone or in combination. Likewise, processing strategies may include multiprocessing, multitasking, parallel processing and the like.

Figure 11:
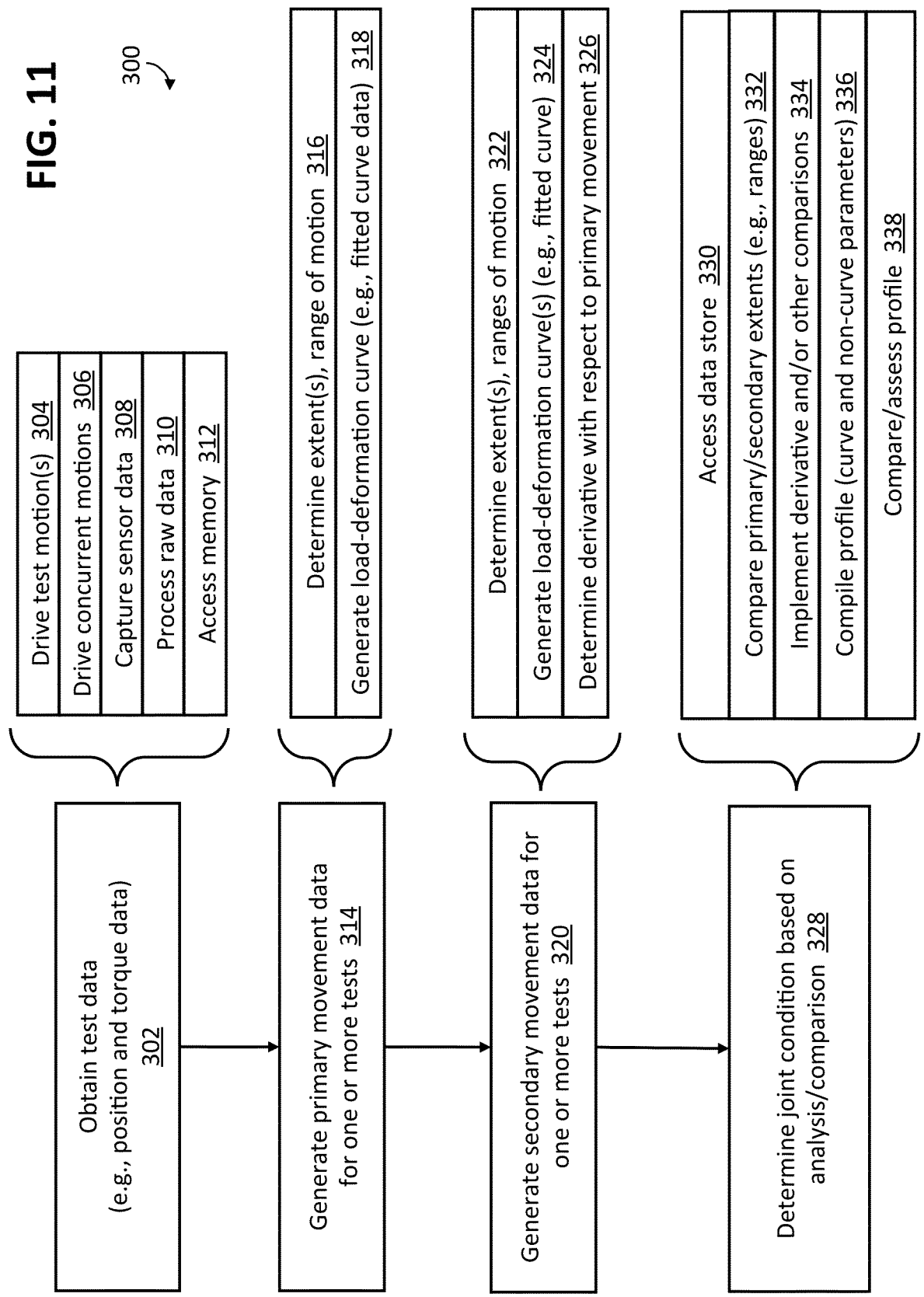
FIG. 11 is a flow diagram of a method for analysis of joints involving multiple independent tests in accordance with one example.

FIG. 11 depicts a method 300 of biomechanical characterization and analysis of knees and other joints. The method 300 is computer-implemented. The method 300 may be implemented by the system 200 of FIG. 10. In some cases, for instance, the processor 212 (FIG. 10) implements one or more acts of the method 300. Alternatively or additionally, the processor 226 (FIG. 10) of the robot testing apparatus 202 implements one or more acts of the method 300. In these cases, the processor 212 and/or the processor 226 are configured via execution of computer-readable instructions, such as the instructions 218, 220, 222 (FIG. 10) stored in the memory 214 (FIG. 10), to cause the processor 212, 226 to implement the method 300. The method 300 may be implemented in additional and/or alternative ways. For instance, one or more acts of the method 300 may be implemented by a remote processor, such as a processor in communication with the processor 212 and/or the processor 226.

The method 300 includes an act 302 in which test data for a joint under test is obtained. The test data is representative of the response of the joint to forces (e.g., torques) applied or imparted in one or more rotational or translational tests. The joint testing is implemented by a robotic testing apparatus applied to the joint, such as the apparatus described above. The robotic test apparatus may be configured to apply or impart a range of forces to the joint and utilize sensors to gather the test data. The sensors may include position sensors and torque sensors. The test data may accordingly include position data and torque data. Additional or alternative types of data may be acquired. For instance, the data may be indicative of a displacement for a given force or torque level. In cases in which the joint is a knee, the rotational movement may be or include varus-valgus rotational movement of the knee and/or external-internal rotational movement of the knee.

The forces are applied or imparted during each joint test in one or more degrees of freedom. Each applied or imparted force in each joint test may be oriented in a respective plane. As described above, each joint test may be characterized by referring to these degree(s) of freedom and plane(s) as primary degree(s) of freedom and primary plane(s) for the joint test. The movement that arises from the applied or imparted forces in the other degrees of freedom may be characterized as secondary or concomitant movement.

The manner in which the load-deformation data is obtained may vary. The act 302 may include the acquisition and/or processing of raw sensor data in an act 304 in which the primary and secondary movement for the joint test(s) is driven by the robotic test apparatus. In some cases, one or more joint tests are implemented in an act 306 in which concurrent motions are driven. For example, a joint test may attempt to mimic the pivot shift test in which force is imparted or applied in multiple planes or degrees of freedom. Sensor data is then captured in an act 308. As described above, obtaining the test data may include the processing of the raw sensor data in an act 310. For instance, the raw sensor data may be processed via one or more coordinate system transformations. Alternative or additional data processing may occur, including, for instance, interpolation. In other cases, the raw sensor data has already been captured, processed, and/or otherwise obtained, in which case the load-deformation data is obtained by accessing a memory in an act 312. One or more data processing steps of the act 310 may follow the memory access of the act 312.

After the test data is obtained, primary movement data is generated for the joint test(s) in an act 314. The primary movement data is indicative of the movement in the primary degree(s) of freedom, e.g., the degree of freedom disposed within the respective plane in which the force of the joint test is oriented. In some cases, generating the primary movement data includes determining in an act 316 the extent or range of motion in the primary degree of freedom or respective plane. Additional or alternative displacement data may be determined for the primary degree(s) of freedom or respective planes.

In some cases, generating the primary movement data includes generating load-deformation data in an act 318 for the primary degree(s) of freedom or respective plane(s). The load-deformation data may be generated by pairing or associating the position data with the force (e.g., torque) data for the primary degree(s) of freedom or respective plane (or one of the other degrees of freedom or planes). In the example of FIG. 11, the load-deformation data includes load-deformation curve data derived from the underlying load-deformation data. The act 318 may, for example, include generating or defining a load-deformation curve function fitted to the load-deformation data. Fitted curve data may then be generated from the load-deformation curve function. The load-deformation curve data may include the data defining the load-deformation curve (e.g., curve parameters, such as PCA factors or polynomial coefficients) and/or the data points defined via the load-deformation curve.

The method 300 also includes generating secondary movement data for the joint test(s) in an act 320. The secondary movement data is indicative of the concomitant movement in one of the secondary degree(s) of freedom that nonetheless arises from the applied or imparted force(s). The secondary degree(s) of freedom may be any degree of freedom other than the degree(s) of freedom disposed in the plane of the test(s). The secondary movement data may be generated for one or more degrees of freedom for one or more joint tests. As with the primary movement data, generating the secondary movement data may include determining a range or extent of motion or other concomitant displacement for the secondary degree(s) of freedom in an act 322 and/or generating load-deformation data, such as load-deformation curve data, in an act 324. The act 320 may alternatively or additionally include characterizing the secondary movement relative to the primary movement. In the example of FIG. 11, the derivative of the secondary movement with respect to the primary movement is determined in an act 326. Additional or alternative derivative data may be determined. For example, the derivative of the secondary movement with respect to the applied force or time may be determined.

The manner in which load-deformation curve data is generated for the primary and secondary movement data may vary. Various types of fitting procedures may be implemented. The fitting may be based on a subset of the load-deformation data as described above. For instance, an unloaded portion of the load-deformation data may be excluded from the subset. The underlying load-deformation data may be divided into hysteresis subsets in preparation for separate fittings. The data points in one or both hysteresis subsets may be adjusted, e.g., via interpolation, to provide common data points for averaging to address the hysteresis.

The nature of the load-deformation curve data for the primary and secondary movement data may vary. In some cases, the load-deformation curve data includes the principal components of the underlying load-deformation data obtained via principal component analysis (PCA) of the load-deformation data. Any number of principal components, or PCA factors, may be generated. One or more of the principle components of the load-deformation data may help identify various biomechanical characteristics of the joint under test. The overall health of joint, or particular injuries or ailments affecting the functioning of the joint may thus be identified.

Additional or alternative characteristics of the load-deformation curve functions may be quantified for use as the primary and secondary movement data. For instance, the quantified features may be a shape (e.g., a quantity representative of the shape) of the load-deformation curve, one or more slopes of the curve, one or more endpoints of the curve, and/or the width of the curve (e.g., at a zero torque level). When the quantified feature is the slope of the curve defined by the load-deformation curve, the slope may be determined at a zero torque level of the curve defined by the load-deformation curve function. In some cases the slope is determined at an endpoint of the curve defined by the load-deformation curve function. In other cases the slope is determined within the last twenty percent of data points before the endpoints of the load-deformation curve data are reached. A variety of other quantities may be determined, including, for instance, the second derivatives of the curves.

A condition of the joint under the test is determined in an act 328 based on an analysis of the primary movement data for the test(s) and the secondary movement data for one or more of the test(s). The joint condition may be or include a biomechanical characteristic indicative of an injury or other abnormality of the joint. The analysis may be used to assess any condition or status of the joint. The act 328 may include accessing in an act 330 a data store, such as the database 224 (FIG. 10), to obtain preset data for comparison with the primary and secondary movement data.

The analysis of the act 328 may include various types of analyses. The type of analysis varies with the nature of the primary and secondary movement data. In some cases, determining the joint condition includes comparing the primary and secondary extents or ranges of motion or other displacement for the joint under test with preset thresholds or other data for those joint test(s) in an act 332. Alternatively or additionally, derivative or other load-deformation curve data is compared with preset data in an act 334. The preset data may include or involve one or more thresholds, distributions, or other data for comparison.

The analysis of the act 328 is not limited to comparisons. For instance, the analysis may include detecting a pattern of the load-deformation curve(s). Various pattern recognition procedures may be implemented.

The primary and secondary movement data may be analyzed collectively. For instance, the comparisons may be implemented as a group. Collective analysis may be useful in circumstances in which one particular test alone is not configured to detect a particular condition. But the particular condition is nonetheless detectable via analysis of the primary data for multiple tests and/or secondary data for one or more tests. In some cases, the act 328 includes compilation of a profile in an act 336. As described above, the profile may include the primary and secondary data, such as curve parameters and non-curve parameters, as well as the results of one or more comparisons with the preset data. The profile may include still further data, including non-test parameters for the joint under test, including, for instance, various parameters of the joint, such as bone size, shape, etc., and various parameters of the subject, such as height, weight, etc. The profile may then be compared or otherwise assessed in an act 338. For instance, preset data indicative of the profiles of various abnormal joints (and/or normal joints) may be compared with the profile compiled for the joint under test.

The methods described herein may be implemented by software programs executable by a computer system. Further, implementations may include distributed processing, component/object distributed processing, and parallel processing. Alternatively or additionally, virtual computer system processing may be constructed to implement one or more of the methods or functionality as described herein.

Described above are joint assessment methods and systems that analyze off-axis or secondary movement. During a particular joint test (e.g., internal-external rotation), position data and force (e.g., torque) data is collected in the plane of the primary motion while torque is applied to the joint in the primary motion plane. Position and force data is also collected in the other two degrees of rotational freedom, i.e., the off-axis rotations (e.g., abduction/adduction and flexion/extension). The other three degrees of freedom (e.g., medial/lateral translation, anterior/posterior translation, and compression/distraction translation) may be positional only or be associated with a force calculated or otherwise determined from an associated torque sensor and its distance from the joint. These motions and forces not in the direction or plane of the primary applied motion are referenced herein as secondary or off-axis motions and forces, and used to assess joint condition (e.g., identify ligament or other injuries) as described above.

As described above, load-deformation curve and other data indicative of movement along various combinations of the six degrees of freedom (i.e., X-axis translation, X-axis rotation, Y-axis translation, Y-axis rotation, Z-axis translation, and Z-axis rotation) is generated for one or more joint tests. The primary motion of a bone of the joint (e.g., the tibia for a knee joint) occurs along or about the axis on or about the load or torque is applied. In one knee joint example in which the load is applied to the tibia distal to the foot and around the tibial Z-axis, the primary motion is internal and external rotation of the tibia around the tibial Z-axis. The secondary motions during that joint test are in the other five degrees of freedom (i.e., other than Z-axis rotation). In some cases, the load-deformation curve data is generated for all six degrees of freedom (e.g., position in the respective degree of freedom as a function of applied force or torque). All six load-deformation curves may then be combined into a dataset that describes the kinetic or kinematic function or performance of the joint under test. The dataset is unique to that joint, but can be compared with the datasets for other joints (e.g., joints with known conditions) to assess or determine the condition or status of the joint under test.

In some cases, each load-deformation curve is used as, and representative of, a principal component in the analysis of the function or performance of the joint under test. Each principal component may thus be a two-dimensional dataset (e.g., a two-dimensional plot). Alternatively or additionally, each principal component includes one or more data points representative of the two-dimensional dataset (e.g., one or more first or second derivatives of the load-deformation curve). Thus, from each of the two-dimensional load-deformation curve plots, a single feature or family of features may be extracted. The extracted feature(s) collectively describe the respective principal component. The collection of the extracted features across the multiple load-deformation curves can then be analyzed to determine the condition of the joint (e.g., identify one or more ligament injuries). For instance, the collection of features can be applied as a set of operands to a rule set (e.g., a Boolean tree) configured to determine the ligament injury or other joint condition.

As described above, in some cases, the joint condition determination is based on the information from multiple joint tests. The multiple tests may provide information indicative of joint function for (e.g., along or about) three independent axes. The independence of the axes provides a full picture of the knee function or performance. In contrast, information for only a single axis may, standing alone, not provide sufficient information to assess joint condition. In some knee joint examples, for instance, the information from three tests (e.g., external-internal rotation, anterior-posterior translation, and varus-valgus rotation) is used. The data indicative of the secondary (or concomitant, off-axis) movement in one or more of the tests may then supplement the primary movement data from the tests to provide a more complete picture of joint function or performance.

The computer-readable media referenced above may be a single medium or multiple media, such as a centralized or distributed database, and/or associated caches and servers that store one or more sets of instructions. The term "computer-readable medium" may also include any tangible medium that may be capable of storing, encoding or carrying a set of instructions for execution by a processor or that may cause a computer system to perform any one or more of the methods or operations disclosed herein. Such computer-readable media may be referred to as "computer-readable storage media."

The computer-readable medium may include a solid-state memory such as a memory card or other package that houses one or more non-volatile read-only memories. The computer-readable medium also may be a random access memory or other volatile re-writable memory. Additionally, the computer-readable medium may include a magneto-optical or optical medium, such as a disk or tapes or other storage device. A digital file attachment to an e-mail or other self-contained information archive or set of archives may be considered a distribution medium that may be a tangible storage medium. Accordingly, the disclosure may be considered to include any one or more of a computer-readable medium or a distribution medium and other equivalents and successor media, in which data or instructions may be stored.

Alternatively or additionally, dedicated hardware implementations, such as application specific integrated circuits, programmable logic arrays and other hardware devices, may be constructed to implement one or more of the methods described herein. Applications that may include the apparatus and systems of various embodiments may broadly include a variety of electronic and computer systems. One or more embodiments described herein may implement functions using two or more specific interconnected hardware modules or devices with related control and data signals that may be communicated between and through the modules, or as portions of an application-specific integrated circuit. Accordingly, the present system may encompass software, firmware, and hardware implementations.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding only, and no unnecessary limitations should be understood therefrom, as modifications within the scope of the invention may be apparent to those having ordinary skill in the art.

What is claimed is:

1. A method comprising:
   capturing test data using a robotic testing apparatus for a joint during a plurality of joint tests, the test data being representative of respective motion of the joint during each test of the plurality of tests, each test of the plurality of test being implemented by the robotic testing apparatus applied to the joint, the robotic testing apparatus being configured to apply, during each test of the plurality of tests, a respective force oriented in a respective plane;
   generating, by a processor, based on the test data, respective primary data representative of respective movement of the joint in a respective degree of freedom for the joint disposed within the respective plane for each test of the plurality of tests, wherein at least one test of the plurality of tests is alone not configured to detect a condition of the joint such that the respective primary data for the at least one test is not indicative of the condition;
   generating, by the processor, based on the test data, secondary data representative of concomitant movement of the joint during a first test of the plurality of tests, the concomitant movement being in a secondary degree of freedom for the joint other than the respective degree of freedom disposed within the respective plane for the first test, the concomitant movement arising from the respective applied force; and
   determining, by the processor, the condition of the joint based on an analysis of the primary data for each test of the plurality of tests and the secondary data,
   wherein the secondary degree of freedom is different than the respective degree of freedom for the first test.

2. The method of claim 1, wherein the respective forces of the plurality of tests are directed to cause anterior-posterior translation, internal-external rotation, and varus-valgus rotation.

3. The method of claim 1, wherein the respective movement in the respective plane of the first test is anterior-posterior translation.

4. The method of claim 1, wherein the respective movement in the respective plane of the first test is internal-external rotation.

5. The method of claim 1, wherein the respective movement in the respective plane of the first test is varus-valgus rotation.

6. The method of claim 1, wherein the secondary data is representative of an extent of concomitant displacement of the joint in the secondary degree of freedom.

7. The method of claim 6, wherein the analysis comprises a comparison of the extent of displacement with a threshold.

8. The method of claim 1, wherein determining the condition comprises:
   compiling a profile for the joint based on the primary data and the secondary data;
   accessing a data store in which preset profile data for abnormal joints is stored; and
   comparing the profile with the preset profile data to determine the condition of the joint.

9. The method of claim 1, wherein the secondary data is representative of a derivative of position of the concomitant movement in the secondary degree of freedom with respect to position in the respective degree of freedom disposed within the respective plane for the first test.

10. The method of claim 1, wherein the concomitant movement in the secondary degree of freedom is disposed in a different plane than the respective plane for the first test.

11. The method of claim 1, wherein:
   the test data comprises position data and torque data;
   generating the respective primary data comprises generating first load-deformation curve data for the movement of the joint in the respective degree of freedom for the joint disposed within the respective plane;
   generating the secondary data comprises generating second load-deformation curve data for the concomitant movement of the joint in the second degree of freedom; and
   determining the condition comprises analyzing the first and second load-deformation curve data.

12. The method of claim 1, wherein:
   the test data comprises position data and torque data for the concomitant movement; and
   the secondary data is representative of a torque level in the secondary degree of freedom, the torque level arising from the imparted force.

13. A method comprising:
  capturing test data using a robotic testing apparatus for a knee joint during an anterior-posterior translation test, an external-internal rotation test, and a varus-valgus rotation test, each of which being implemented by the robotic testing apparatus applying a respective force to the joint;
  generating, by a processor, based on the test data, respective primary data representative of respective primary movement of the joint during the anterior-posterior translation test, the external-internal rotation test, and the varus-valgus rotation test;
  generating, by the processor, based on the test data, secondary data representative of concomitant movement of the joint during one or more of the anterior-posterior translation test, the external-internal rotation test, and the varus-valgus rotation test, the concomitant movement arising from the respective applied force; and
  determining, by the processor, a condition of the joint based on an analysis of the respective primary data for the anterior-posterior translation test, the external-internal rotation test, and the varus-valgus rotation test, and of the secondary data,
  wherein, for each of the anterior-posterior translation test, the external-internal rotation test, and the varus-valgus rotation test, the primary movement and the concomitant movement are in different degrees of freedom.

14. The method of claim 13, wherein the secondary data is representative of an extent of the concomitant movement.

15. The method of claim 14, wherein the analysis comprises a comparison of the extent of the concomitant movement with a threshold.

16. The method of claim 15, wherein determining the condition comprises:
  compiling a profile for the joint, the profile comprising a result of the comparison;
  accessing a data store in which preset profile data for abnormal joints is stored; and
  comparing the profile with the preset profile data to determine the condition of the joint.

17. The method of claim 13, wherein the secondary data is representative of a derivative of position of the concomitant movement with respect to position in the primary movement.

18. The method of claim 13, wherein the concomitant movement is disposed in a different plane than the respective primary movement of a test during which the concomitant movement occurs.

19. A system comprising:
  a robotic testing apparatus configured to capture test data for a knee joint during a plurality of joint tests;
  a memory in which input instructions, data processing instructions, and analysis instructions are stored; and
  a processor coupled to the memory and configured through execution of the input instructions to obtain the test data captured by the robotic testing apparatus, the test data being representative of respective motion of the joint during each test of the plurality of tests, each test of the plurality of tests being implemented by the robotic testing apparatus applied to the joint, the robotic testing apparatus being configured to apply, during each test of the plurality of tests, a respective force oriented in a respective plane;
  wherein the processor is configured through execution of the data processing instructions to generate, based on the test data, respective primary data representative of respective movement of the joint in a respective degree of freedom for the joint disposed within the respective plane for each test of the plurality of tests, and to generate, based on the test data, secondary data representative of concomitant movement of the joint during a first test of the plurality of tests, the concomitant movement being in a secondary degree of freedom for the joint other than the respective degree of freedom disposed within the respective plane for the first test, the concomitant movement arising from the respective applied force,
  wherein the processor is configured through execution of the analysis instructions to determine a condition of the joint based on an analysis of the primary data for each test of the plurality of tests and the secondary data, and
  wherein the secondary degree of freedom is different than the respective degree of freedom for the first test.

20. The system of claim 19, wherein the plurality of joint tests comprise an anterior-posterior translation test, an external-internal rotation test, and a varus-valgus rotation test.

21. The system of claim 20, wherein the concomitant movement is off-axis movement occurring during the anterior-posterior translation test.

22. The system of claim 20, wherein the concomitant movement is off-axis movement occurring during the varus-valgus rotation test.

* * * * *